United States Patent
Saito

(10) Patent No.: US 12,185,913 B2
(45) Date of Patent: Jan. 7, 2025

(54) ENDOSCOPE CAP AND ENDOSCOPE

(71) Applicant: HOYA CORPORATION, Tokyo (JP)

(72) Inventor: Keiichi Saito, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 472 days.

(21) Appl. No.: 17/626,999

(22) PCT Filed: Nov. 10, 2020

(86) PCT No.: PCT/JP2020/041818
§ 371 (c)(1),
(2) Date: Jan. 13, 2022

(87) PCT Pub. No.: WO2021/100537
PCT Pub. Date: May 27, 2021

(65) Prior Publication Data
US 2022/0248942 A1    Aug. 11, 2022

(30) Foreign Application Priority Data
Nov. 19, 2019 (JP) .................................. 2019-209048

(51) Int. Cl.
*A61B 1/00* (2006.01)

(52) U.S. Cl.
CPC ...... *A61B 1/00137* (2013.01); *A61B 1/00098* (2013.01)

(58) Field of Classification Search
CPC ............ A61B 1/00137; A61B 1/00098; A61B 1/018; A61B 1/0011; A61B 1/00101;
(Continued)

(56) References Cited

U.S. PATENT DOCUMENTS 5,725,477 A    3/1998 Yasui et al.
2018/0317741 A1 * 11/2018 Yamaya ................. G02B 23/24
(Continued)

FOREIGN PATENT DOCUMENTS

JP    07-148107    6/1995
JP    2018-126487    8/2018
(Continued)

OTHER PUBLICATIONS

International Search Report issued in International Bureau of WIPO Patent Application No. PCT/JP2020/041818, dated Jan. 19, 2021, along with an English translation thereof.

*Primary Examiner* — Timothy J Neal
*Assistant Examiner* — James Edward Boice
(74) *Attorney, Agent, or Firm* — GREENBLUM & BERNSTEIN, P.L.C.

(57) ABSTRACT

To provide an endoscope cap includes: a cover having a cylindrical shape with a bottom; a pedestal; and an elevator rotatably supported by the pedestal. The pedestal includes: a base; a support wall, rising from an edge of the base, and extending in an axial direction of the cover to support the elevator; a distal tip wall extending from a distal tip of the support wall in the same direction as the base; a bottom fixing protrusion protruding from the distal tip wall in a direction opposite to the support wall; and a lateral face fixing protrusion protruding from the base in a direction opposite to the support wall. The cover includes: a first fixing hole into which the bottom fixing protrusion is inserted, being disposed in the bottom; and a second fixing hole into which the lateral face fixing protrusion is inserted, being disposed in a lateral face.

7 Claims, 25 Drawing Sheets

(58) Field of Classification Search
CPC .............. A61B 1/0623; A61B 1/00128; A61B 1/00087; A61B 8/12
USPC ........................................................ 600/107
See application file for complete search history.

(56) References Cited

U.S. PATENT DOCUMENTS

2019/0117045 A1  4/2019  Hosogoe
2019/0223697 A1  7/2019  Hosogoe et al.

FOREIGN PATENT DOCUMENTS

WO      2018/016484     1/2018
WO      2018/070515     4/2018

\* cited by examiner

FIG. 5
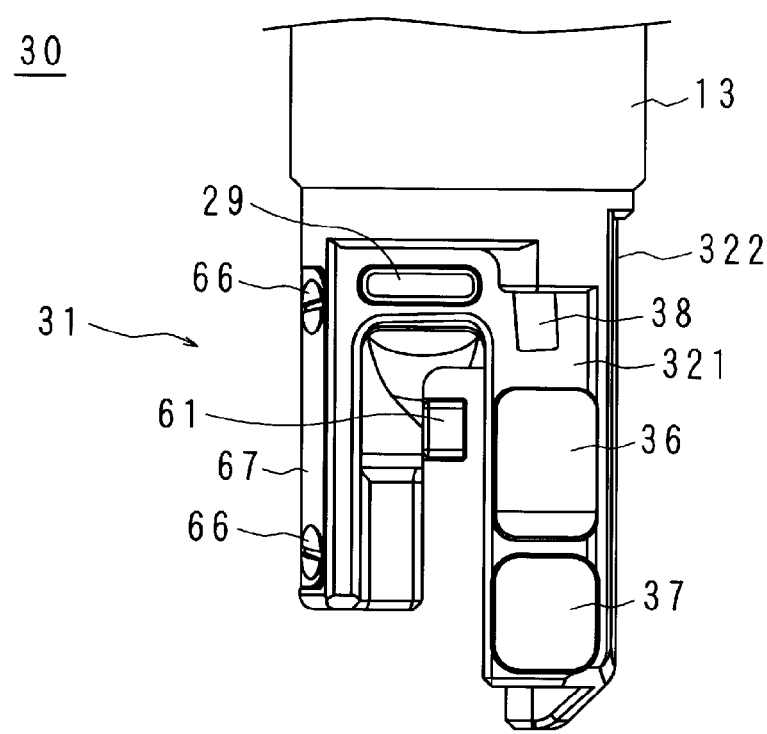
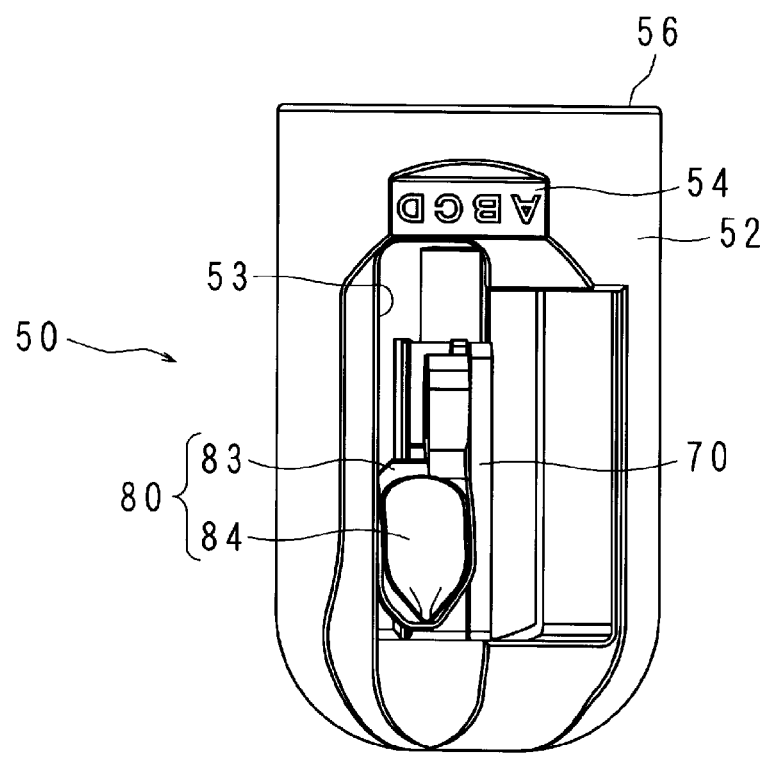

ENDOSCOPE CAP AND ENDOSCOPE

TECHNICAL FIELD

The present invention relates to an endoscope cap and an endoscope.

BACKGROUND ART

A known endoscope includes an elevator at a distal tip of a channel passing through the inside of an insertion portion. The elevator is used to curve a treatment tool or the like inserted through the channel and to guide the treatment tool in a desired direction.

There has been proposed an endoscope cap provided with an elevator which is mounted on a distal tip of an endoscope before endoscopic examination and dismounted after the endoscopic examination (Patent Literature 1). Since the complicated structure around the elevator can be dismounted from the endoscope, it is possible to clean the endoscope easily.

CITATION LIST

Patent Literature

Patent Literature 1: WO 2018/070515 A

SUMMARY OF INVENTION

Technical Problem

The endoscope cap disclosed in Patent Literature 1 has a three-body structure: a cover, an elevator, and a pedestal. An elevator shaft disposed in the elevator is inserted into an elevator mounting hole disposed in the pedestal, thereby rotatably supporting the elevator. The pedestal that supports the elevator is fixed to a pedestal groove disposed in an inner surface of the cover.

Endoscope caps are desirably so-called "single-use" caps. Single-use endoscope caps to be supplied to medical institutions are packaged individually. Compared with endoscopes well known as precision instruments, endoscope caps are subjected to impacts during transportation and storage.

It is not possible to use an endoscope cap having a cover and a pedestal come off due to an impact. The pedestal and the cover should be mounted again or another endoscope cap should be prepared, which puts a burden on a user. Similarly, in mounting an endoscope cap on an endoscope, when a cover and a pedestal come off the endoscope cap, a user bears a burden.

A single-use endoscope cap is dismounted from an endoscope after the end of a case analysis. During the dismounting, when a cover and a pedestal come off, small components such as the pedestal may scatter. The scattering of a component to which a body fluid is attached imposes a burden on a user. For example, the user is required to search for the scattered component and disinfect the place where the scattered component has fallen.

In an aspect of the invention, an object is to provide an endoscope cap and the like including a cover and a pedestal that hardly come off.

Solution to Problem

An endoscope cap detachably attached to an insertion portion of an endoscope, the endoscope cap including: a cover having a cylindrical shape with a bottom, and being detachably attached to a distal tip of the insertion portion from an opening end portion; a pedestal held inside the cover; and an elevator rotatably supported by the pedestal, in which the pedestal includes: a base having a tabular shape, being disposed in an inner surface of a cylindrical portion of the cover; a support wall having a tabular shape, rising from an edge of the base, and extending in an axial direction of the cover to support the elevator; a distal tip wall extending from a distal tip of the support wall in the same direction as the base; a bottom fixing protrusion protruding from the distal tip wall in a direction opposite to the support wall; and a lateral face fixing protrusion protruding from the base in a direction opposite to the support wall, and the cover includes: a first fixing hole into which the bottom fixing protrusion is inserted, the first fixing hole being disposed in the bottom; and a second fixing hole into which the lateral face fixing protrusion is inserted, the second fixing hole being disposed in a lateral face.

Advantageous Effects of Invention

An aspect of the invention provides an endoscope cap and the like including a cover and a pedestal that hardly come off.

BRIEF DESCRIPTION OF DRAWINGS

FIG. 5 is a front view for describing a state before an endoscope cap is mounted on the distal tip of the insertion portion.

DESCRIPTION OF EMBODIMENTS

First Embodiment

Figure 1:
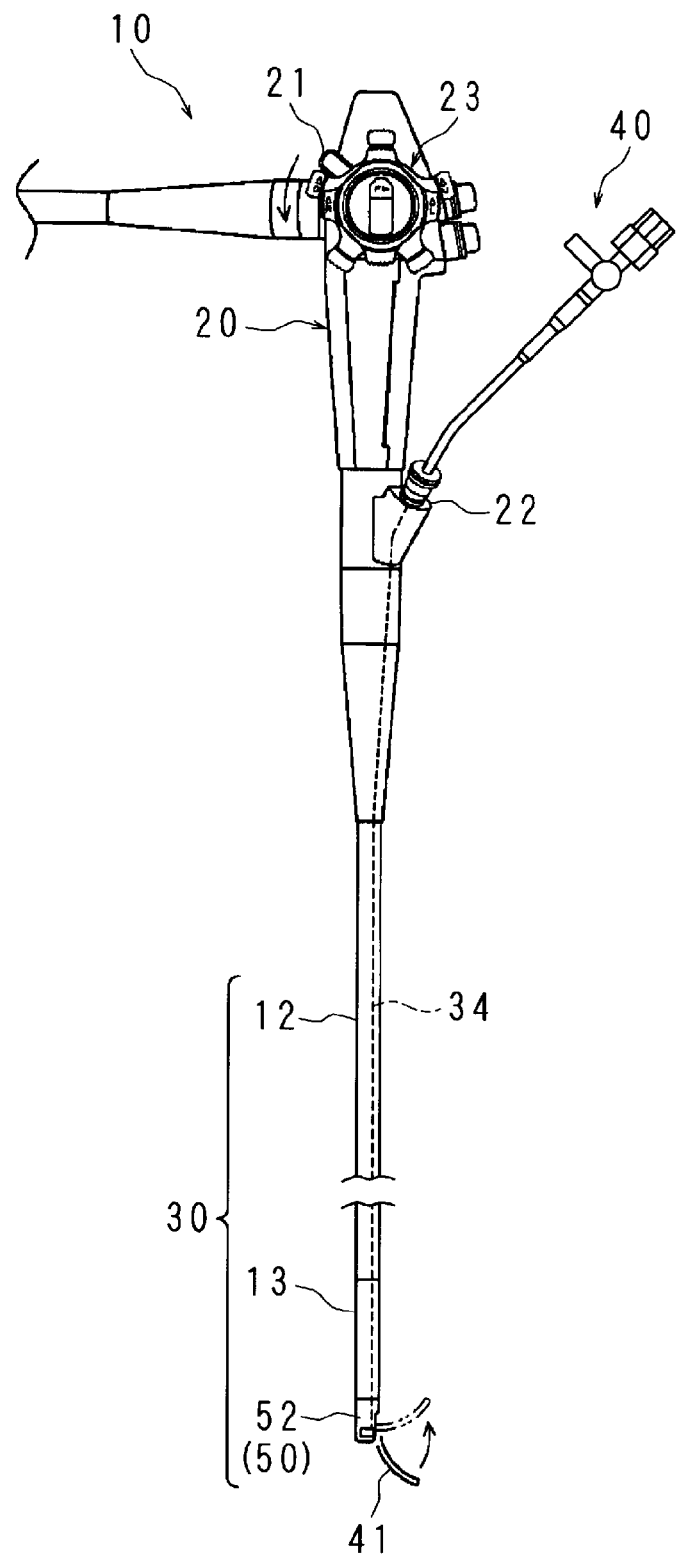
FIG. 1 is an exterior view of an endoscope.

FIG. 1 is an exterior view of an endoscope 10. The endoscope 10 of this embodiment is a flexible scope for an upper gastrointestinal tract. The endoscope 10 includes an operation unit 20 and an insertion portion 30. The operation unit 20 includes an elevation control lever 21, a channel inlet 22, and a bending knob 23. The operation unit 20 is connected to, for example, a video processor, a light source device, and a display device (not illustrated).

The insertion portion 30 is long and has one end connected to the operation unit 20. The insertion portion 30 includes a soft portion 12, a bending section 13, and an endoscope cap 50 in this order from the operation unit 20. The soft portion 12 is long. The bending section 13 bends according to an operation of the bending knob 23. The endoscope cap 50 covers a hard distal tip 31 (see FIG. 2) continuous with the bending section 13.

In the endoscope 10 of this embodiment, the endoscope cap 50 can be detachably attached to the distal tip 31. The endoscope cap 50 includes a cover 52 as an exterior member and an elevator 80 (see FIG. 2). The configuration of the endoscope cap 50 will be described later in detail.

Hereinafter, the longitudinal direction of the insertion portion 30 is referred to as "insertion direction". Similarly, the side closer to the operation unit 20 along the insertion direction is referred to as "the operation unit side", and the side away from the operation unit 20 is referred to as "the distal tip side". For each component, the expressions "the operation unit side" and "the distal tip side" are used according to the direction in which each component is mounted on the endoscope 10.

Figure 2:
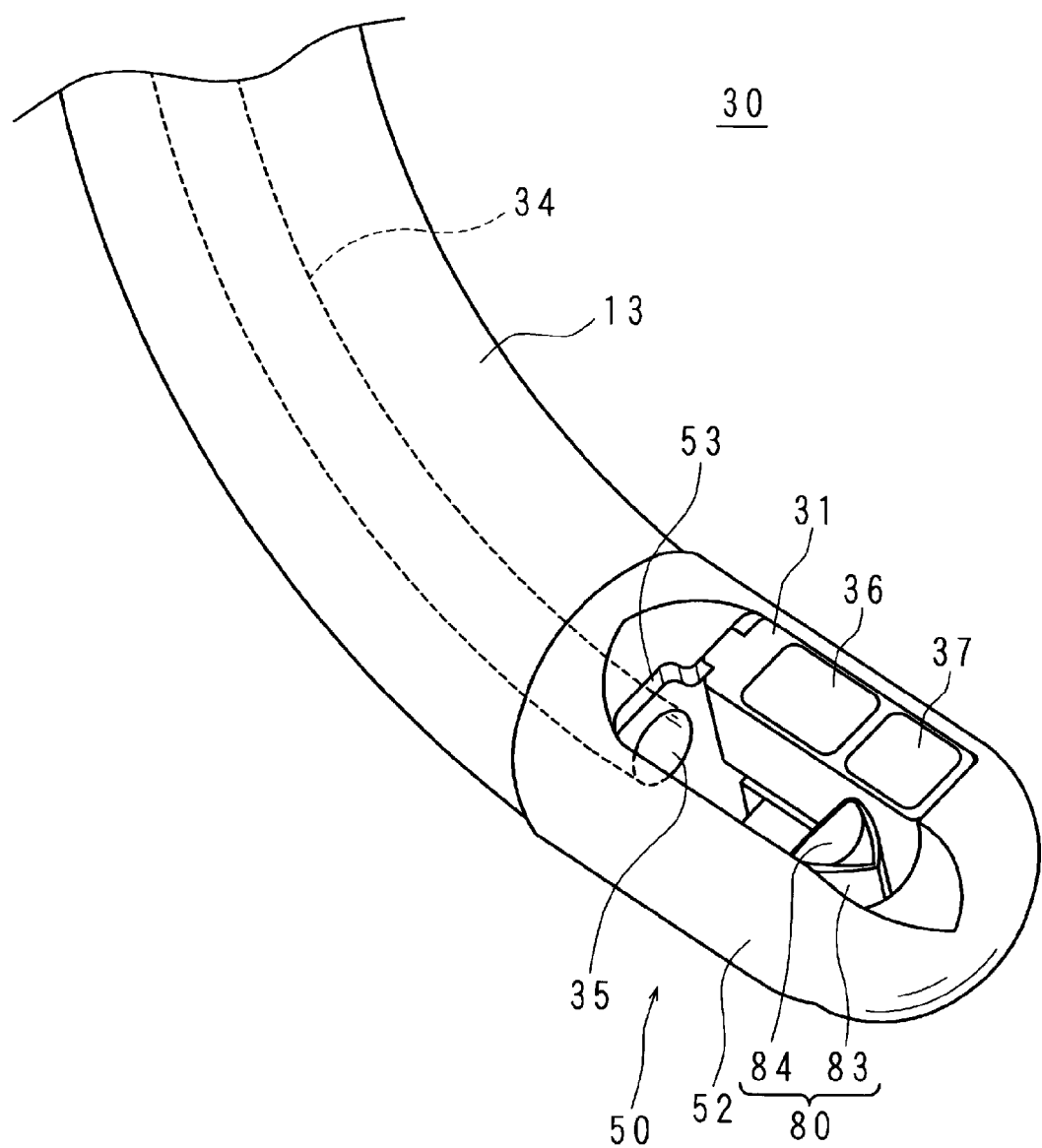
FIG. 2 is a perspective view of a distal tip of an insertion portion.
Figure 3:
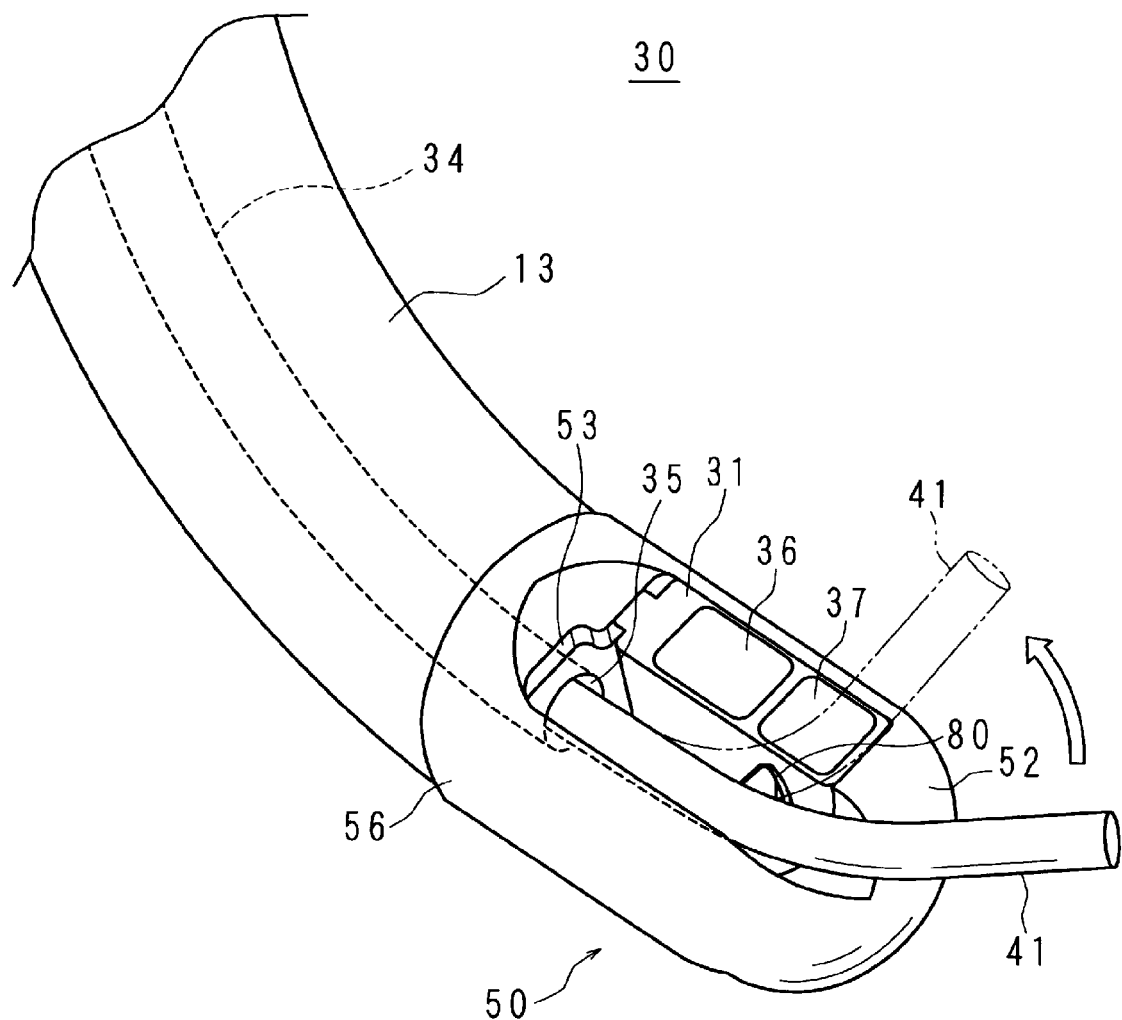
FIG. 3 is a view for describing a state where a treatment tool distal tip protrudes from the distal tip of the insertion portion.

FIG. 2 is a perspective view of a distal tip of the insertion portion 30. FIG. 3 is a view for describing a state where a treatment tool distal tip 41 protrudes from the distal tip of the insertion portion 30. The configuration of the endoscope 10 according to this embodiment will be described with reference to FIGS. 1 to 3.

The distal tip 31 disposed at a distal tip of the bending section 13 includes an observation window 36 and a lighting window 37 aligned on one side along the insertion direction. The lighting window 37 is disposed closer to the distal tip side than the observation window 36. On the opposite side or on the operation unit side, the distal tip 31 includes a channel outlet 35. A raiser 83 is disposed closer to the distal tip side than the channel outlet 35. The cover 52 covering the distal tip 31 has a part provided with a substantially rectangular window 53. The part corresponds to the observation window 36, the lighting window 37, and the raiser 83. A side of the window 53 on the operation unit side is formed into a step. That is, a side of a part including the raiser 83 is closer to the operation unit side, and a side of a part including the observation window 36 is closer to the distal tip side.

The lighting window 37 radiates illumination light emitted from the light source device (not illustrated). It is possible to optically observe a range irradiated with the illumination light through the observation window 36. The endoscope 10 of this embodiment is what is called a side viewing endoscope in which the viewing direction that allows optical observation intersects the insertion direction. The endoscope 10 may be a forward oblique viewing endoscope in which the viewing direction is slightly tilted toward the distal tip side. Alternatively, the endoscope 10 may be a backward oblique viewing endoscope in which the viewing direction is slightly tilted toward the operation unit side.

The channel inlet 22 and the channel outlet 35 are connected by a channel 34 passing through the inside of the soft portion 12 and the bending section 13. A treatment tool 40 is inserted into the channel inlet 22 from the treatment tool distal tip 41, thereby protruding the treatment tool distal tip 41 from the channel outlet 35.

The treatment tool distal tip 41 protrudes while gently curving on the raiser 83 as indicated by the solid line in FIG. 3. When a user operates the elevation control lever 21, a lever 60 (see FIG. 7) moves as will be described later, and the elevator 80 moves in conjunction with the lever 60 as indicated by the arrow in FIG. 1. The movement of the elevator 80 causes the treatment tool distal tip 41 on the elevator 80 to bend toward the operation unit 20 as indicated by the arrows and dash-dot-dot lines in FIGS. 1 and 3. The movement of the treatment tool distal tip 41 is captured by an image sensor or the like (not illustrated) through the observation window 36 and shown on the display device (not illustrated).

The treatment tool 40 is an instrument used for treatment such as a high-frequency knife, a forceps, and a contrast tube. The instrument to be inserted into the channel 34 is not limited to one used for treatment. For example, an instrument used for observation such as an ultrasonic probe and a microscopic endoscope may be inserted into the channel 34. Hereinafter, the instrument used for observation is also referred to as the treatment tool 40.

The movement of the elevator 80 as described above may hereinafter be expressed as "the elevator 80 rises". When the treatment tool distal tip 41 is bent due to a push from the raised elevator 80, such an action is expressed as "the treatment tool 40 rises". A user operates the elevation control lever 21 to adjust the level of the rise of the treatment tool 40.

Figure 4:
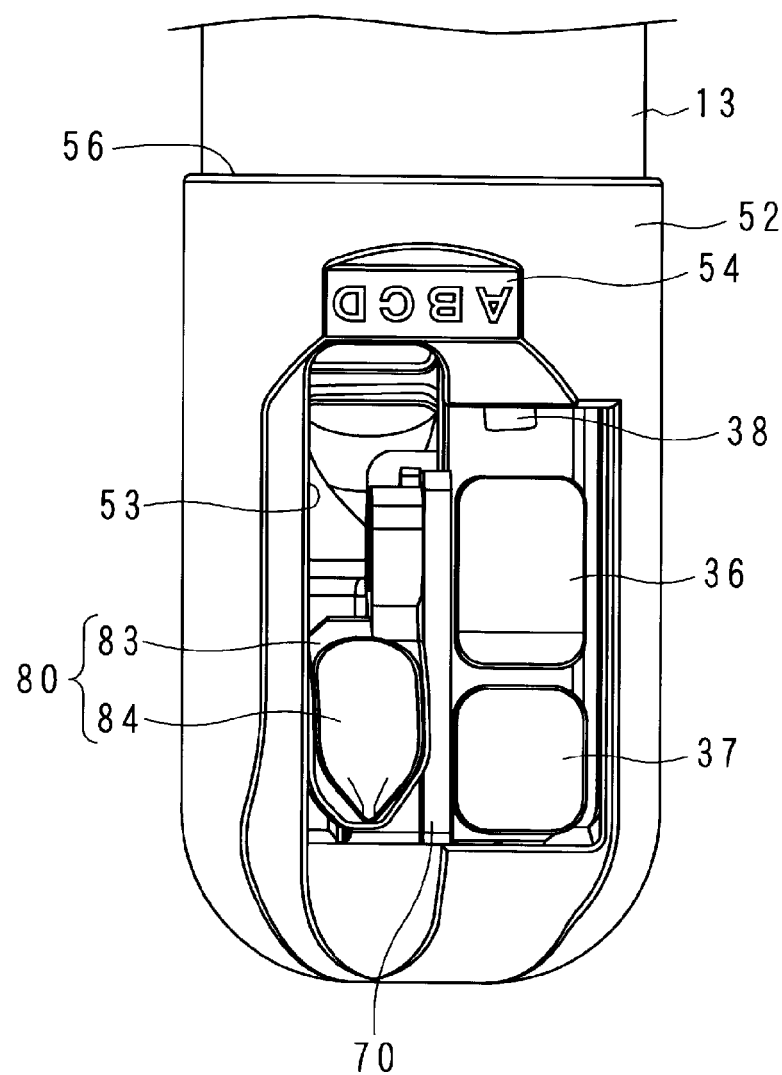
FIG. 4 is a front view of the distal tip of the insertion portion.

FIG. 4 is a front view of the distal tip of the insertion portion 30. The cover 52 has a cylindrical shape with a bottom, having an opening end portion 56 at one end. The cover 52 includes a sign display 54 between the window 53 and the opening end portion 56. For example, a model number of the endoscope cap 50 is shown on the sign display 54. In this embodiment, the cover 52 is manufactured by injection molding, and the model number of the sign display 54 is formed during the molding of the cover 52.

Note that, for example, laser marking may be employed to write characters or barcodes on the sign display 54. In this case, for example, a lot number or a serial number can be individually shown on the cover 52.

FIG. 5 is a front view for describing a state before the endoscope cap 50 is mounted on the distal tip of the insertion portion 30. A user of the endoscope 10 holds the bending section 13 with one hand and pinches the cover 52 with two fingers of the other hand. Opposing the endoscope cap 50 and the distal tip 31 to each other, the user pushes the endoscope cap 50 to mount the endoscope cap 50 on the insertion portion 30.

On completion of endoscopic examination, the user holds the bending section 13 with one hand and presses the right and left lateral faces of the cover 52 in FIG. 5 with two fingers of the other hand to deform the cover 52 slightly. The user pulls the cover 52 toward the distal tip side, thereby dismounting the endoscope cap 50 from the distal tip of the insertion portion 30.

Figure 6:
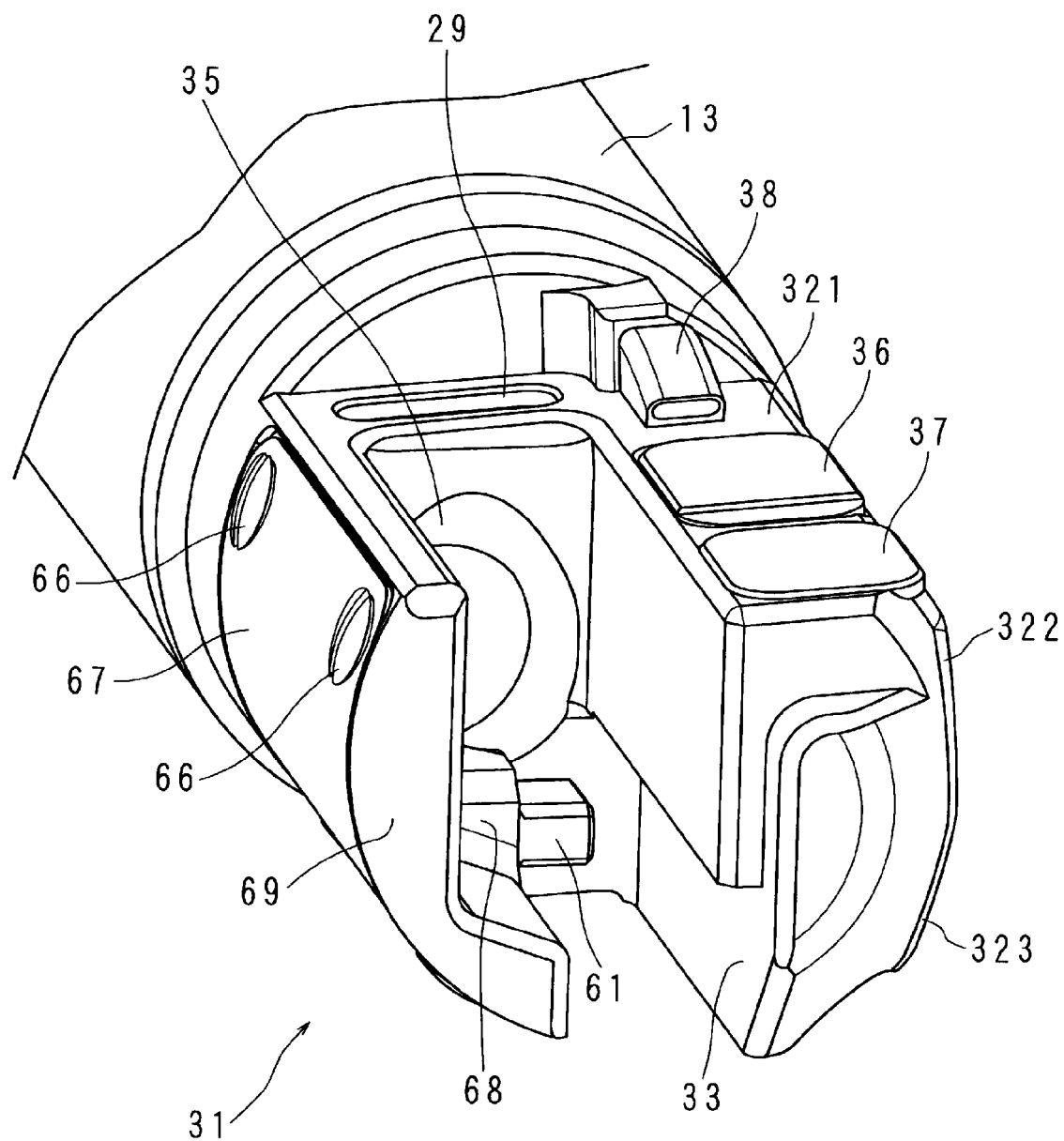
FIG. 6 is a perspective view of the distal tip of the insertion portion before mounting the endoscope cap.

FIG. 6 is a perspective view of the distal tip of the insertion portion 30 before mounting the endoscope cap 50. The configuration of the distal tip of the insertion portion 30 will be described with reference to FIGS. 5 and 6. The distal tip 31 has a substantially columnar shape and is divided into an optical housing portion 33 and a lever chamber 69 by a groove disposed from the distal tip side toward the operation unit side at a position deviated from the center. The channel outlet 35 is open at a bottom of the groove.

A part of the periphery of the distal tip 31 is cut into a flat shape to form a first flat surface 321. On a part of the first flat surface 321, a third engagement portion 29 is disposed along the bottom of the groove that separates the optical housing portion 33 from the lever chamber 69. The third engagement portion 29 is an oval recess.

The observation window 36 and the lighting window 37 are disposed in the first flat surface 321 on the side closer to the optical housing portion 33. The operation unit side of the observation window 36 is provided with a nozzle 38 that sprays water and air to the observation window 36 to clean the observation window 36. On the outer side of the optical housing portion 33, a part of the periphery of the distal tip 31 is cut to form a second flat surface 322 and a third flat surface 323. The second flat surface 322 and the third flat surface 323 are continuous at an angle.

The lever chamber 69 is hollow and covered with a rectangular thin lever chamber lid 67 along the periphery of the distal tip 31. The lever chamber lid 67 is fixed at four corners by lid screws 66. The lever chamber 69 includes a support wall 68 on the side closer to the optical housing portion 33.

From the support wall 68, an elevator connection portion 61 protrudes toward the optical housing portion 33. The elevator connection portion 61 is a shaft having a rectangular cross section. As illustrated in FIGS. 5 and 6, while the endoscope cap 50 is dismounted, the elevator connection portion 61 is exposed on the surface of the distal tip 31.

Figure 7:
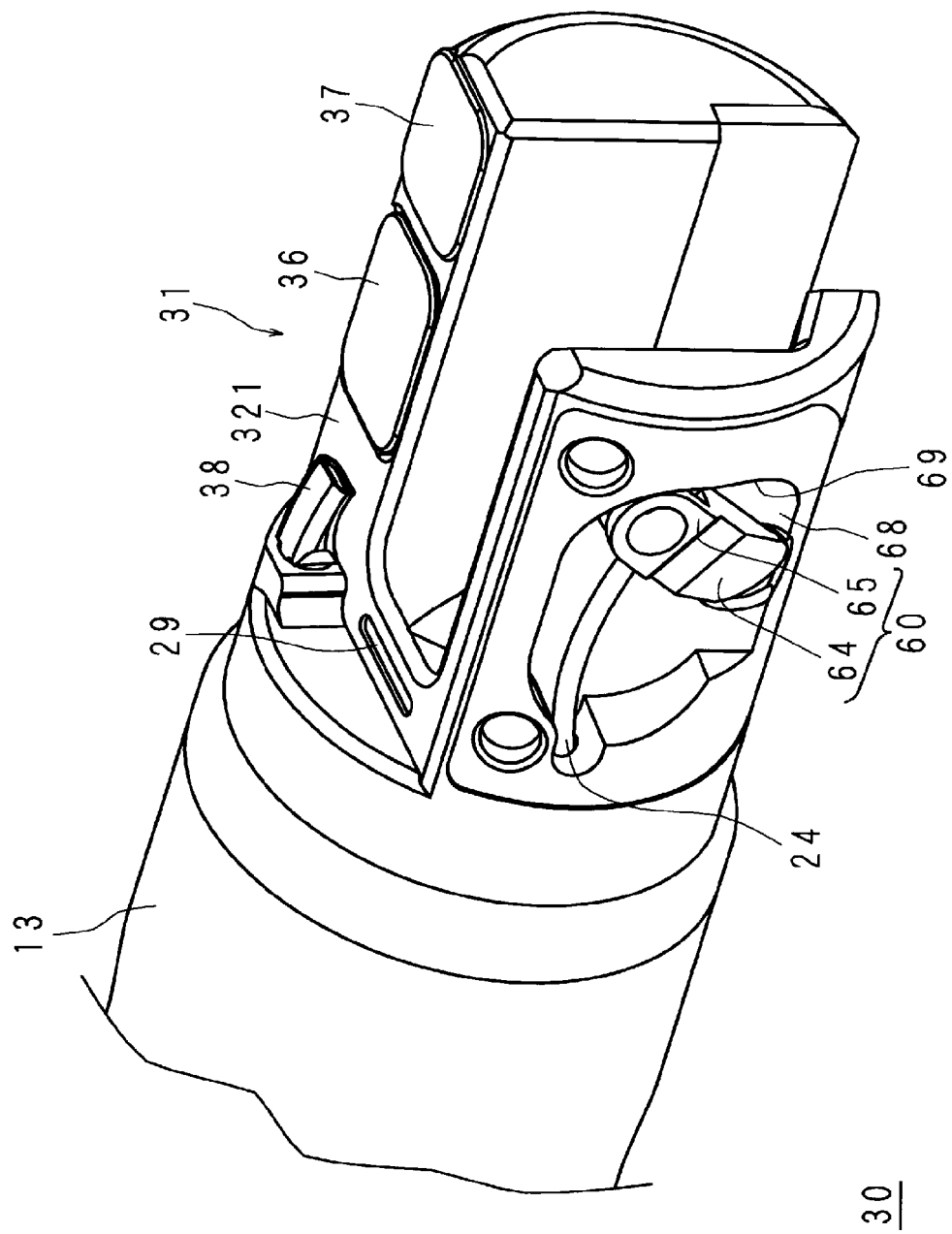
FIG. 7 is a perspective view of the distal tip of the insertion portion from which the endoscope cap and a lever chamber lid are dismounted.

FIG. 7 is a perspective view of the distal tip of the insertion portion 30 from which the endoscope cap 50 and the lever chamber lid 67 are dismounted. The lever 60 is disposed inside the lever chamber 69. The lever 60 includes a wire anchor 65 at one end and the elevator connection portion 61 at the other end via a rotatable connection portion 64. The lever 60 is rotatably supported by a hole disposed in the support wall 68 between the rotatable connection portion 64 and the elevator connection portion 61. The term "rotatable" signifies a rotational motion within a predetermined angle range.

The wire anchor 65 is connected to an end portion of an elevation wire 24. The elevation wire 24 is connected to the elevation control lever 21 through the insertion portion 30 (see FIG. 1). More specifically, the elevation wire 24 is inserted through a guide pipe (not illustrated) having an inner diameter slightly larger than an outer diameter of the elevation wire 24. The guide pipe (not illustrated) passes through the insertion portion 30 in the longitudinal direction. Therefore, a distal tip of the elevation wire 24 moves back and forth in conjunction with the operation of the elevation control lever 21. The elevation wire 24 is remotely operated by the elevation control lever 21.

When a user operates the elevation control lever 21 in a direction indicated by the arrow in FIG. 1, the distal tip of the elevation wire 24 connected to the elevation control lever 21 is pulled toward the operation unit side. The lever 60 is pulled by the elevation wire 24 and rotates.

Figure 8:
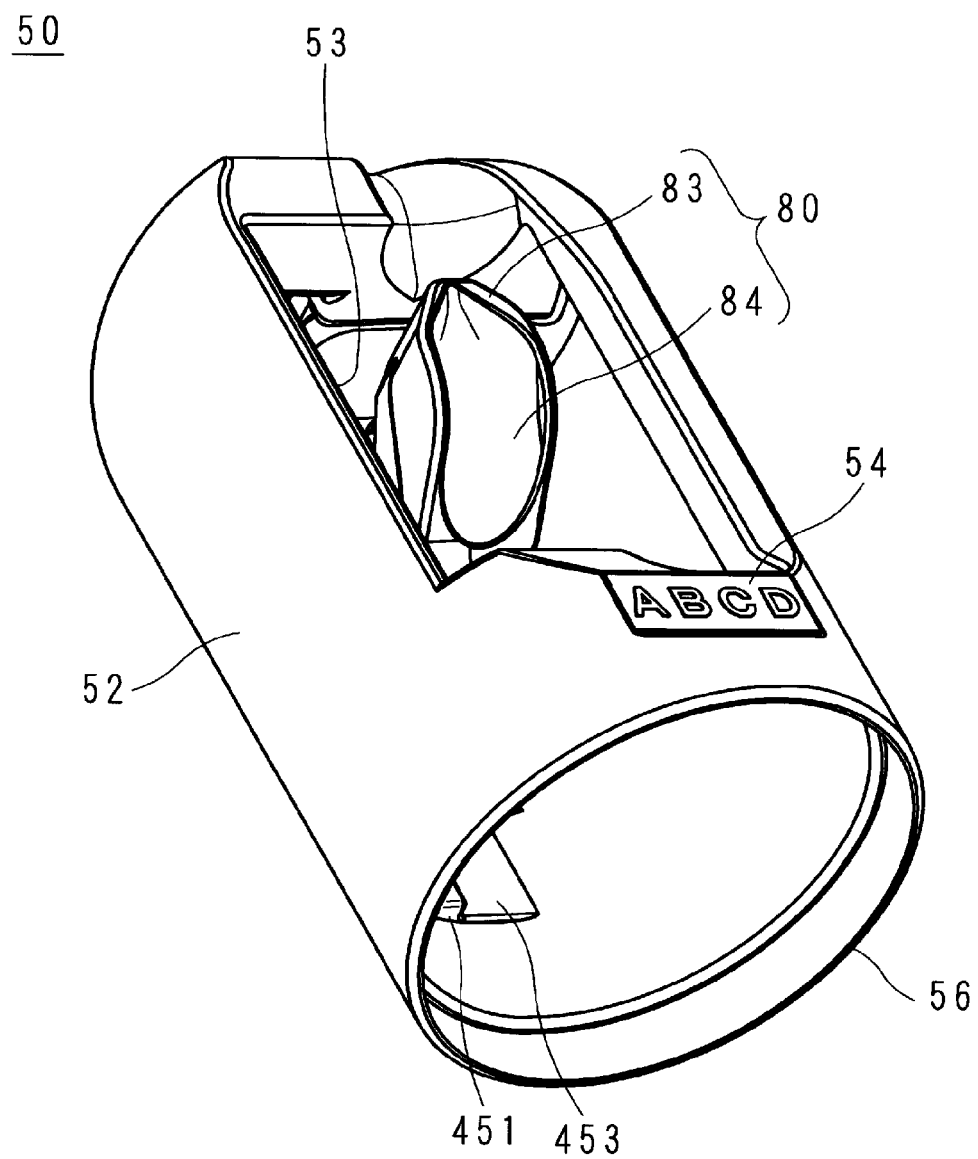
FIG. 8 is a perspective view of the endoscope cap as seen from the side where the endoscope cap is to be mounted on the endoscope.
Figure 9:
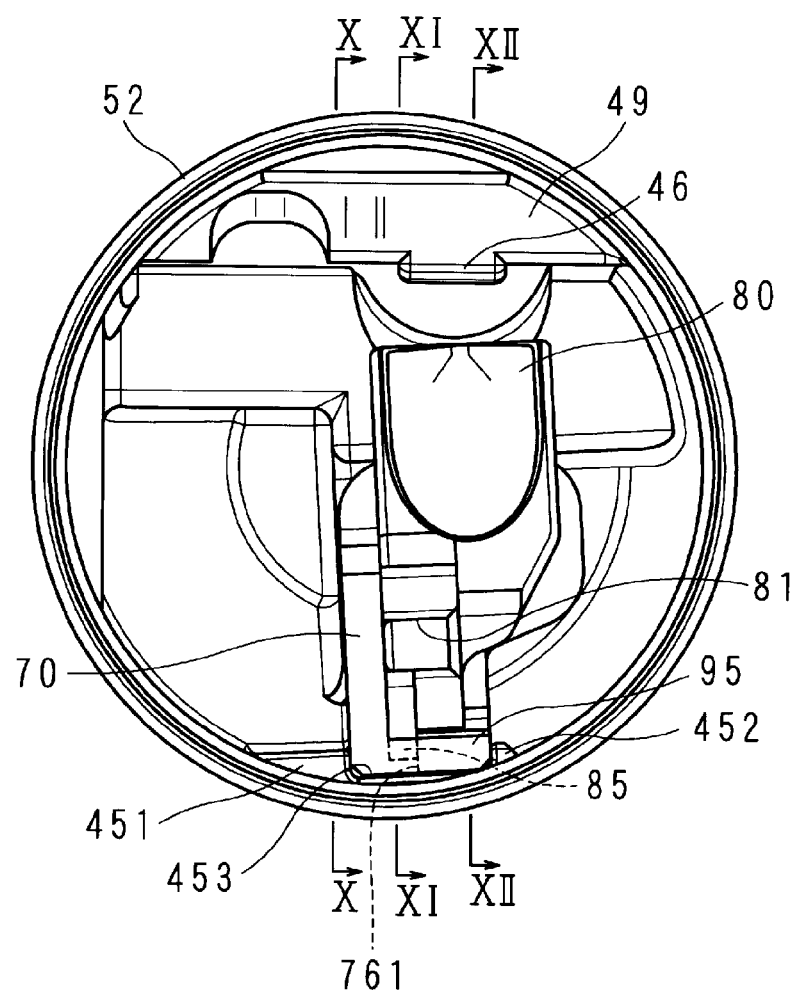
FIG. 9 is a view of the endoscope cap as seen from the side where the endoscope cap is to be mounted on the endoscope.
Figure 10:
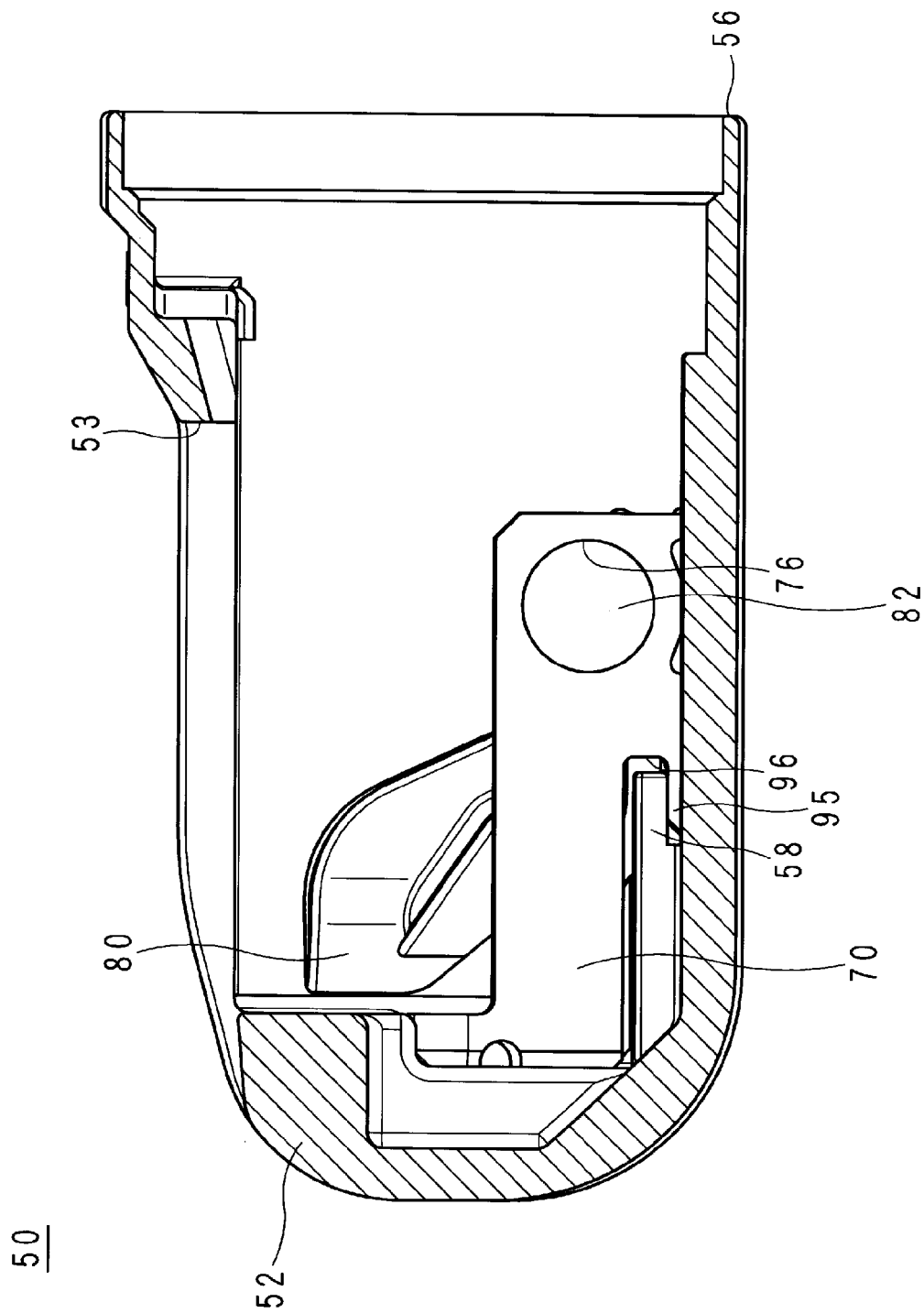
FIG. 10 is a cross-sectional view of the endoscope cap taken along line X-X of FIG. 9.
Figure 11:
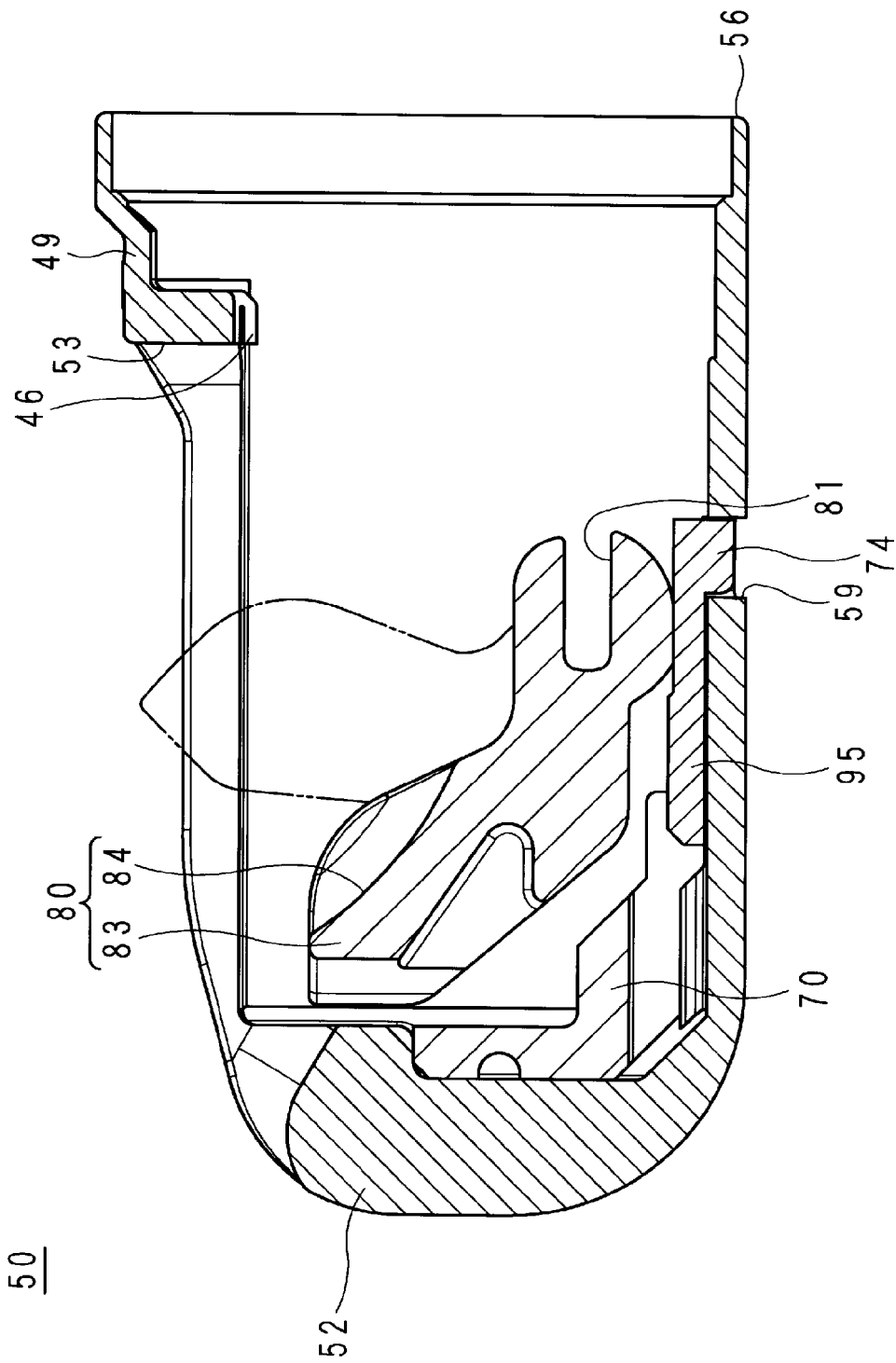
FIG. 11 is a cross-sectional view of the endoscope cap taken along line XI-XI of FIG. 9.
Figure 12:
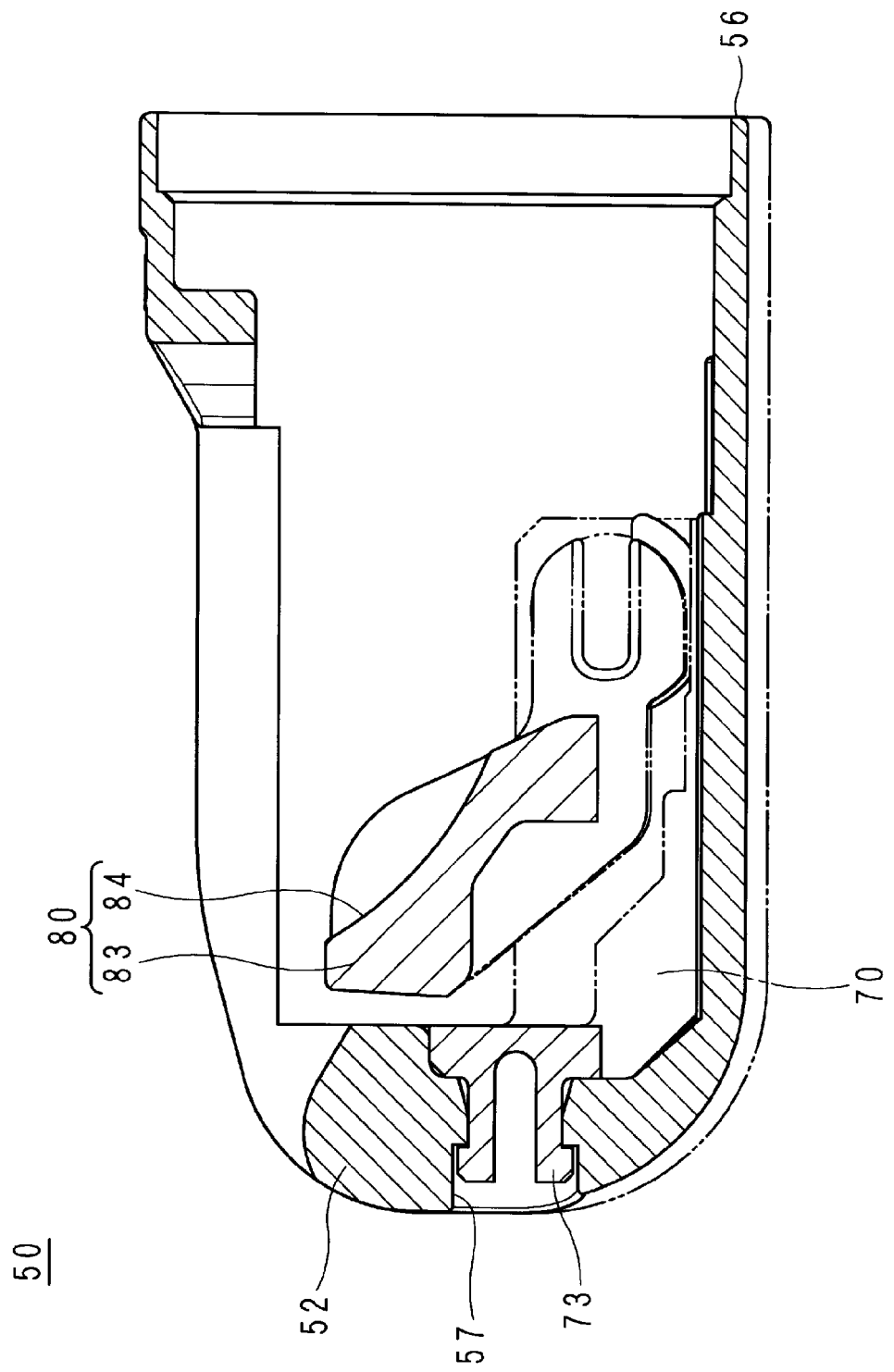
FIG. 12 is a cross-sectional view of the endoscope cap taken along line XII-XII of FIG. 9.

FIG. 8 is a perspective view of the endoscope cap 50 as seen from the side where the endoscope cap 50 is to be mounted on the endoscope 10. FIG. 9 is a view of the endoscope cap 50 as seen from the side where the endoscope cap 50 is to be mounted on the endoscope 10. FIG. 10 is a cross-sectional view of the endoscope cap 50 taken along line X-X of FIG. 9. FIG. 11 is a cross-sectional view of the endoscope cap 50 taken along line XI-XI of FIG. 9. FIG. 12 is a cross-sectional view of the endoscope cap 50 taken along line XII-XII of FIG. 9.

As described above, the endoscope cap 50 includes the cover 52 and the elevator 80. The elevator 80 is rotatably mounted on a pedestal 70. The cover 52 includes the window 53 in the cylindrical portion. At one place on the periphery of the cover 52, the window 53 is opened over almost the entire length. The pedestal 70 is fixed to an inner surface facing the window 53.

As illustrated in FIG. 11, a lateral face fixing protrusion 74 protruding from one end of the pedestal 70 penetrates a second fixing hole 59 penetrating the lateral face of the cover 52. The configurations of the cover 52 and the pedestal 70 will be described later in detail.

Figure 13:
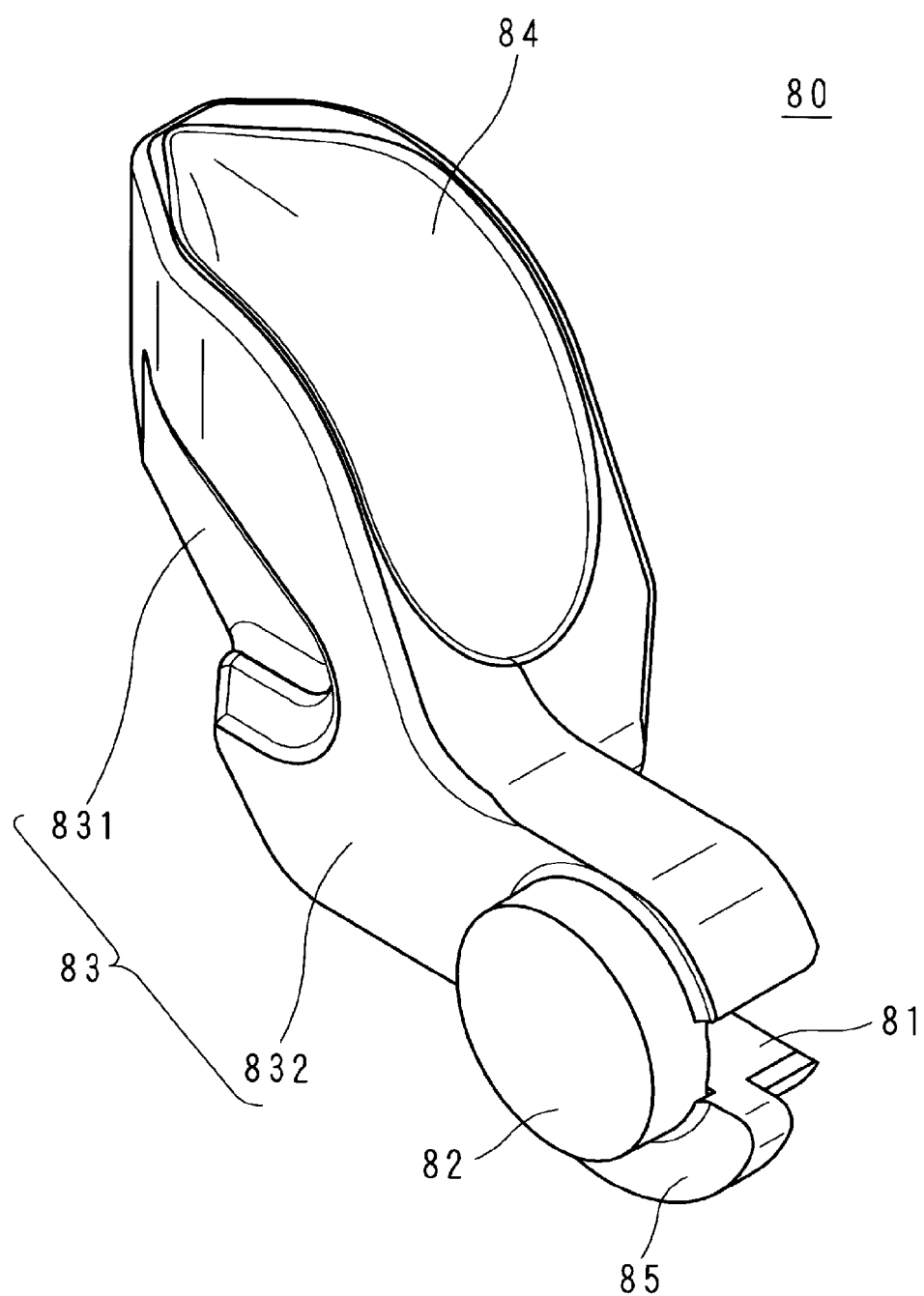
FIG. 13 is a perspective view of an elevator.
Figure 14:
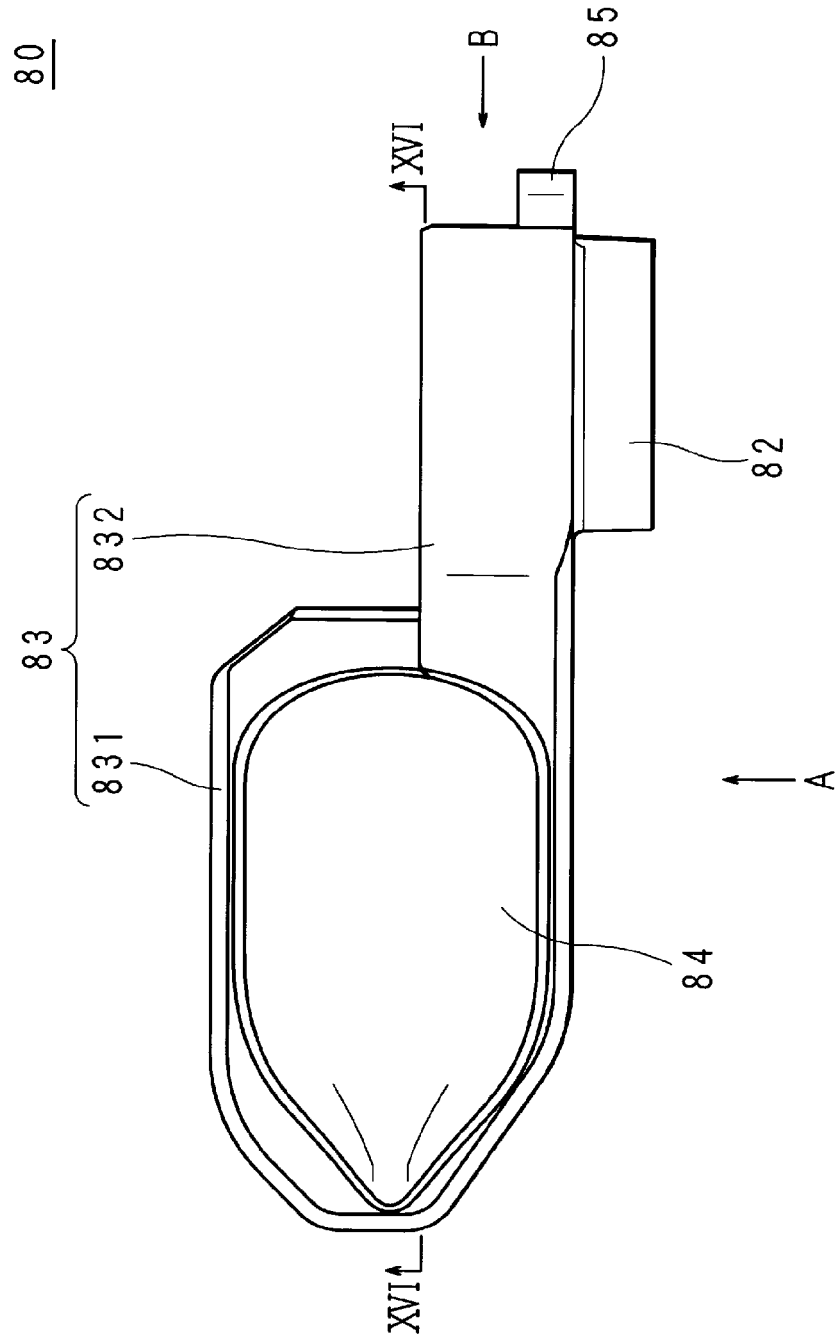
FIG. 14 is a front view of the elevator.
Figure 15:
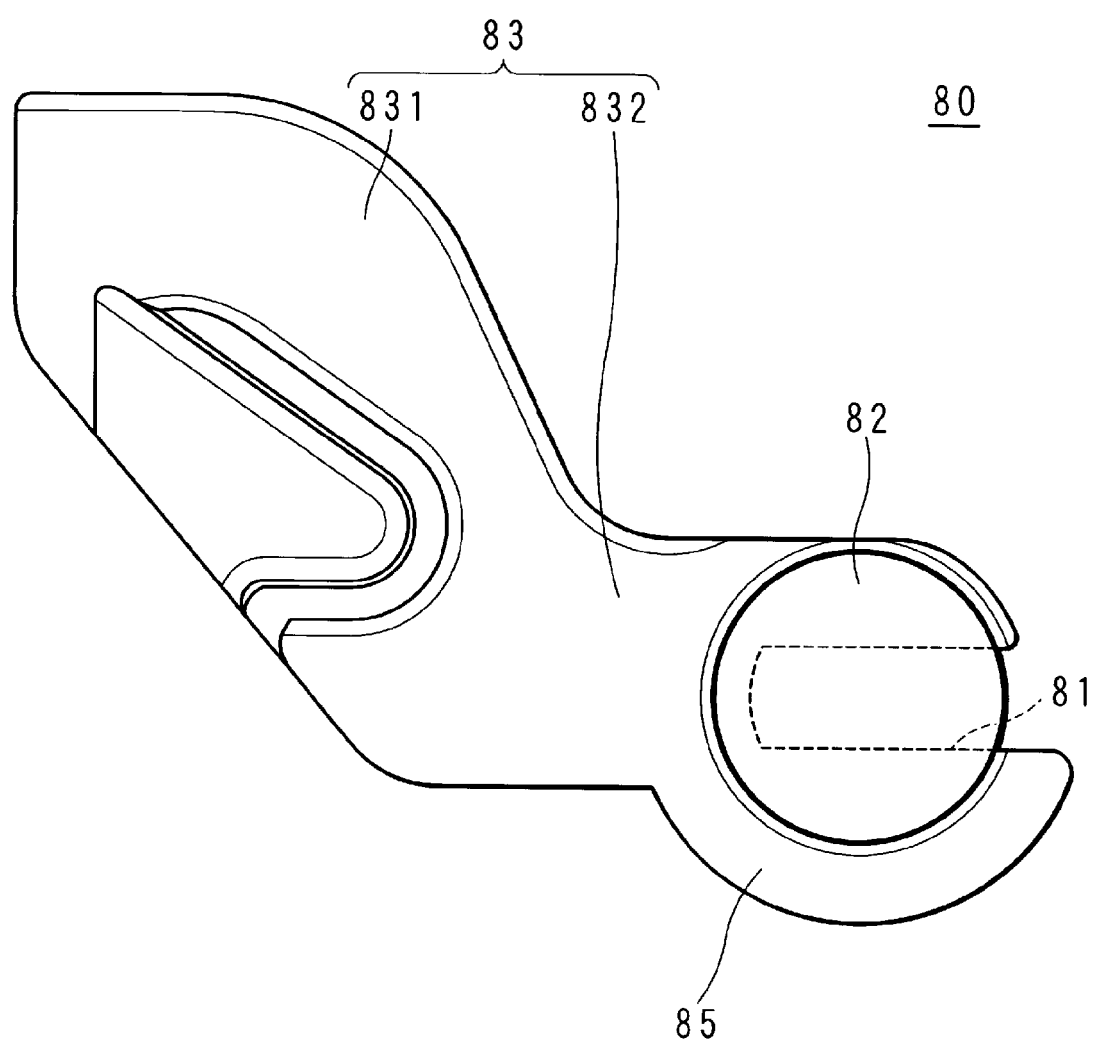
FIG. 15 is a view of the elevator as seen from the direction of A-arrow in FIG. 14.
Figure 16:
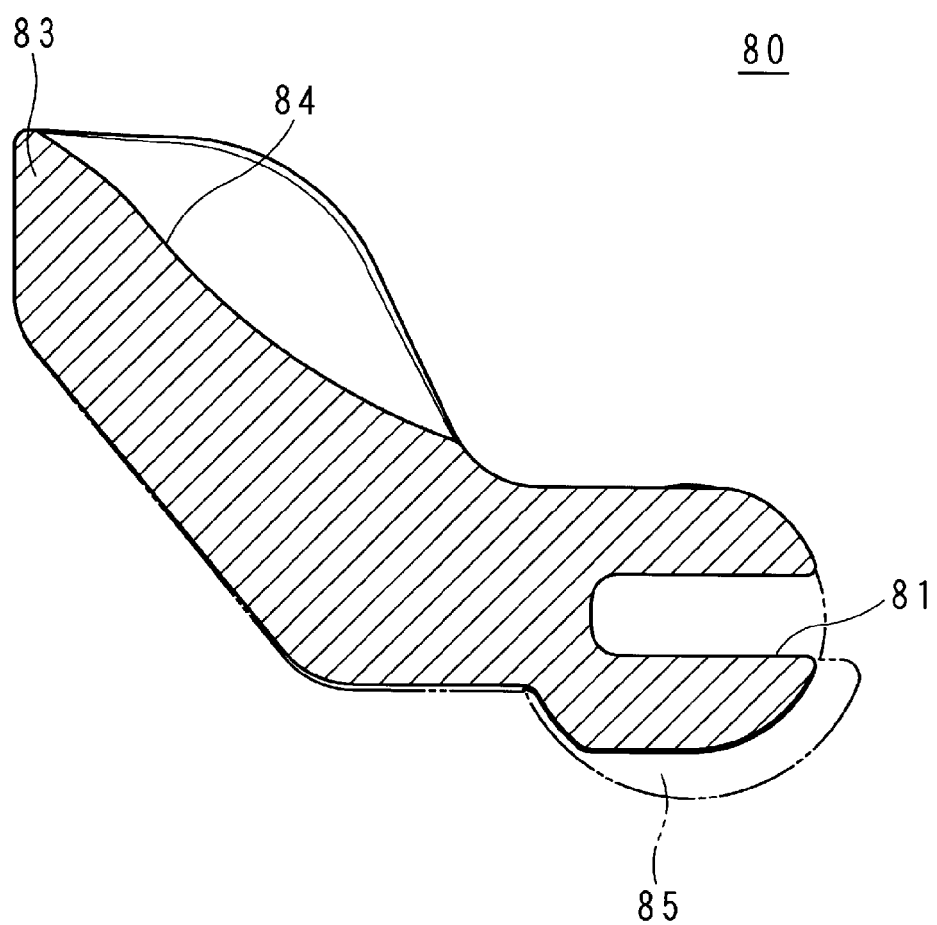
FIG. 16 is a cross-sectional view of the elevator taken along line XVI-XVI of FIG. 14.
Figure 17:
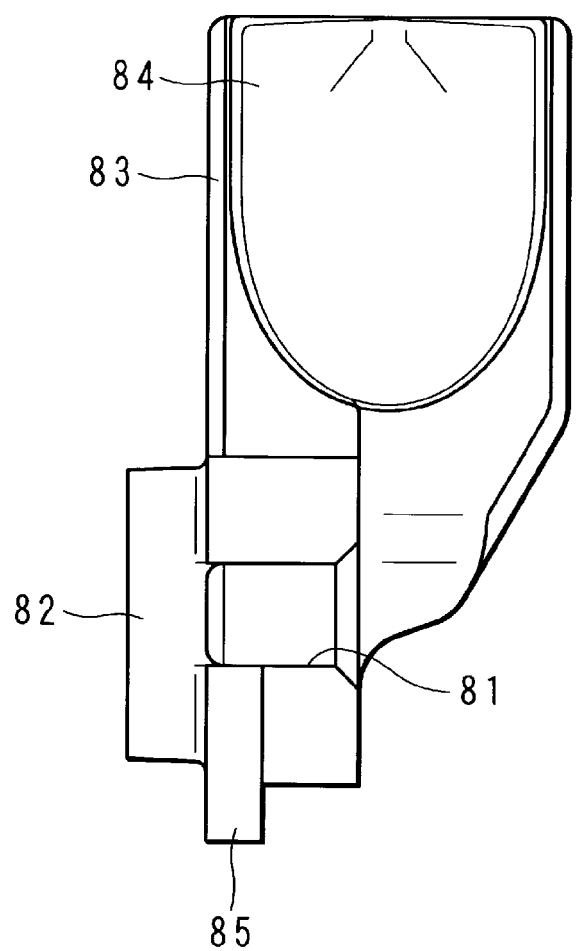
FIG. 17 is a view of the elevator as seen from the direction of B-arrow in FIG. 14.

FIG. 13 is a perspective view of the elevator 80. FIG. 14 is a front view of the elevator 80. FIG. 15 is a view of the elevator 80 as seen from the direction of A-arrow in FIG. 14. FIG. 16 is a cross-sectional view of the elevator 80 taken along line XVI-XVI of FIG. 14. FIG. 17 is a view of the elevator 80 as seen from the direction of B-arrow in FIG. 14. The configuration of the elevator 80 will be described with reference to FIGS. 13 to 17.

The elevator 80 includes a columnar elevator shaft 82 and the raiser 83 protruding from one end face of the elevator shaft 82 substantially perpendicularly to the axial direction of the elevator shaft 82. The raiser 83 has a substantially L shape including a second raiser 832 and a first raiser 831 in this order from the base end.

The second raiser 832 is in contact with the elevator shaft 82 and has a width substantially equal to a diameter of the elevator shaft 82. The first raiser 831 is connected to one end portion of the second raiser 832 at an angle. The first raiser 831 includes a spoon-shaped recess 84 in an inner surface of the L shape.

A lever connection portion 81 is disposed at the other end portion of the second raiser 832. The lever connection portion 81 is a U-shaped groove, opened toward the end portion of the second raiser 832. One edge of the lever connection portion 81 is covered with an end portion of the elevator shaft 82. In the second raiser 832, a part closer to the elevator shaft 82 is partially provided with a tabular flange 85. The flange 85 protrudes toward the outside of the L-shaped elevator 80.

The lever connection portion 81 sandwiches the central axis of the elevator shaft 82 as indicated by the dash line in FIG. 15. A lateral face of the flange 85 has a substantially semi-circular columnar shape substantially coaxial with the elevator shaft 82.

Figure 18:
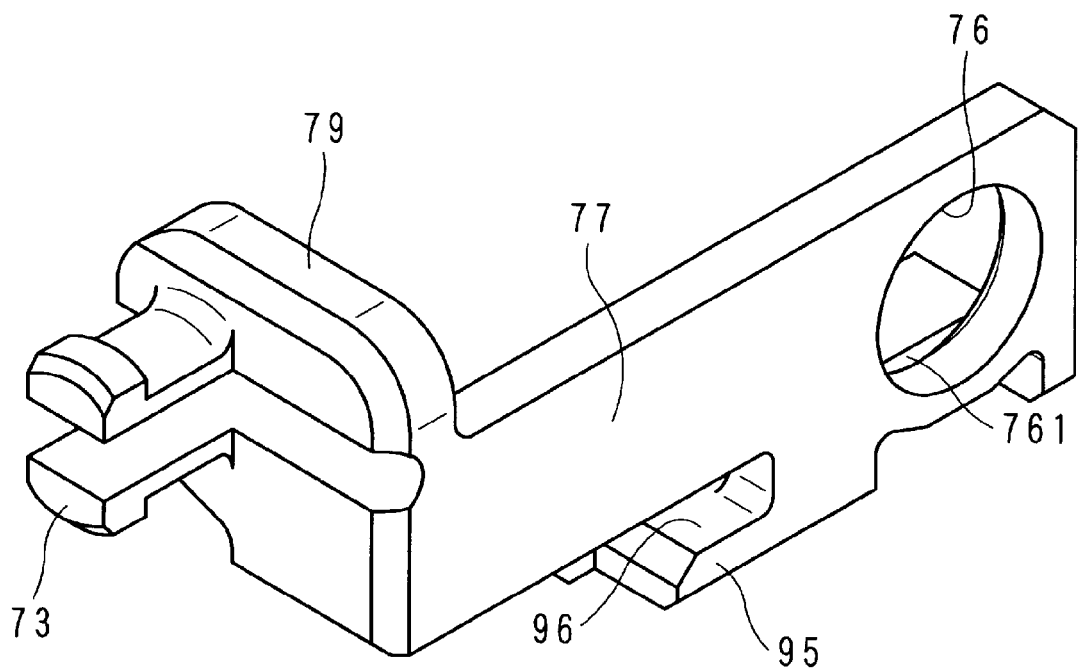
FIG. 18 is a perspective view of a pedestal.
Figure 19:
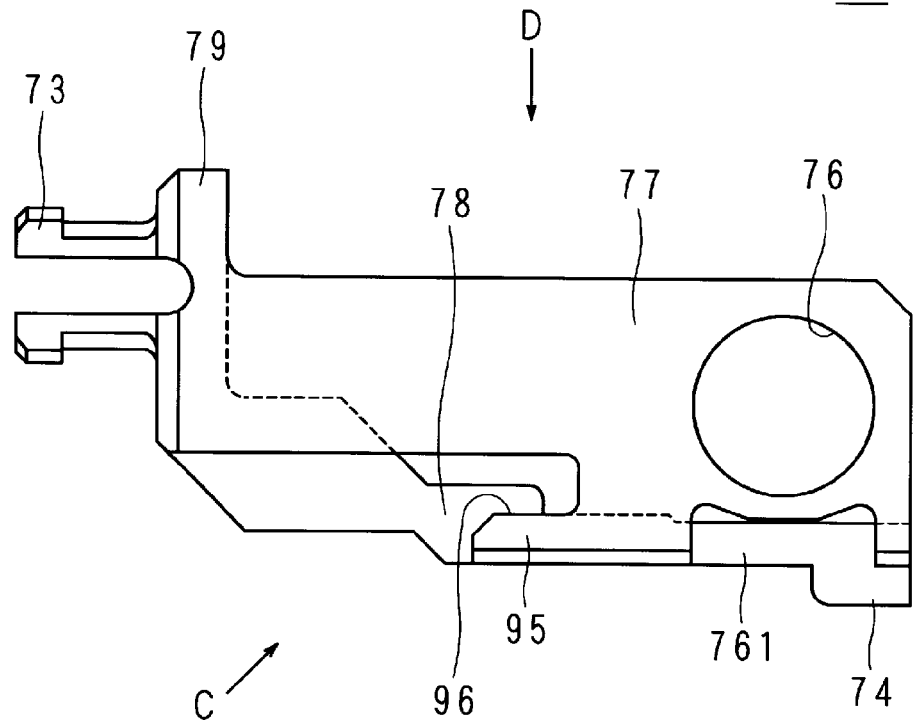
FIG. 19 is a front view of the pedestal.
Figure 20:
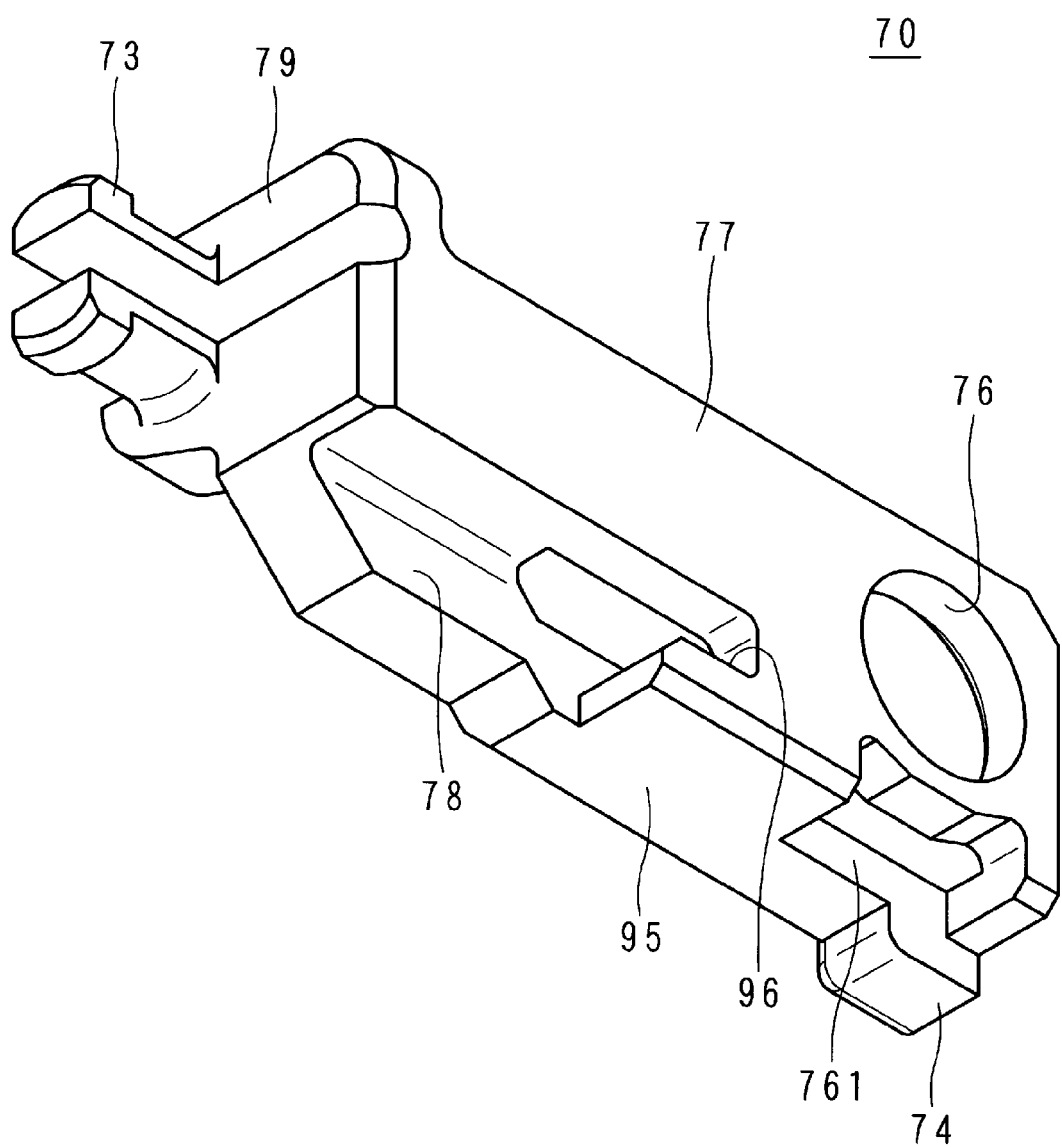
FIG. 20 is a view of the pedestal as seen from the direction of C-arrow in FIG. 19.
Figure 21:
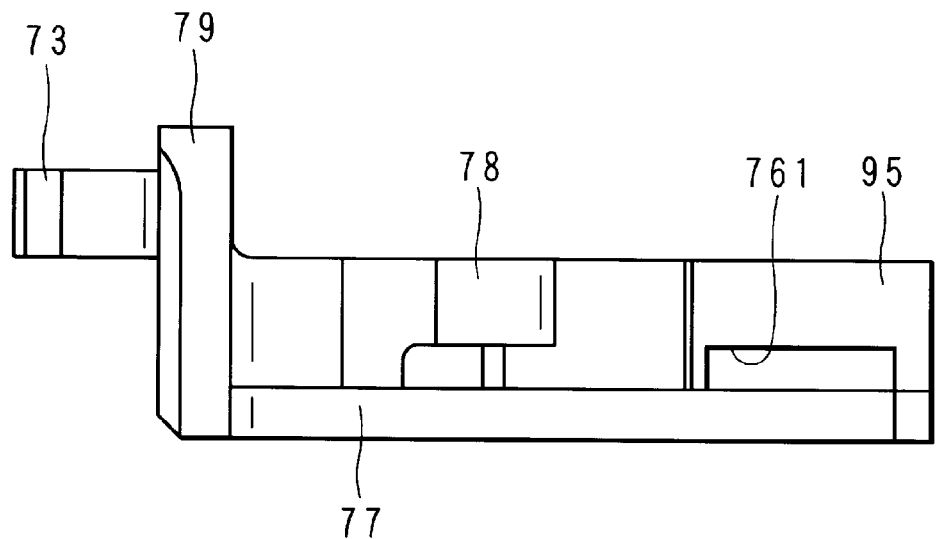
FIG. 21 is a view of the pedestal as seen from the direction of D-arrow in FIG. 19.

FIG. 18 is a perspective view of the pedestal 70. FIG. 19 is a front view of the pedestal 70. FIG. 20 is a view of the pedestal 70 as seen from the direction of C-arrow in FIG. 19. FIG. 21 is a view of the pedestal 70 as seen from the direction of D-arrow in FIG. 19. The configuration of the pedestal 70 will be described with reference to FIGS. 18 to 21.

The pedestal 70 includes a tabular base 95 having a rectangular shape and a tabular first wall 77 having a substantially rectangular shape. The first wall 77 rises from an edge on one of the long sides of the base 95 and extends along the longitudinal direction of the base 95. The first wall 77 is an example of a support wall of this embodiment.

Furthermore, in parallel with the first wall 77, a tabular second wall 78 having a substantially stepped shape with three tiers rises from the base 95. The top tier of the second wall 78 has an end portion to which a rectangular tabular third wall 79 that straddles the first wall 77 and the second wall 78 is connected. The third wall 79 is an example of a distal tip wall of this embodiment.

The third wall 79 is provided with a first fixing protrusion 73 on a surface opposite to the first wall 77. The first fixing protrusion 73 includes a slit. The first fixing protrusion 73 has an end portion provided with a slightly thicker lock. The first fixing protrusion 73 is an example of a bottom fixing protrusion of this embodiment.

In the pedestal 70, the side on which the first fixing protrusion 73 protrudes is the distal tip side, and the opposite side of the first fixing protrusion 73 along the longitudinal direction of the first wall 77 is the operation unit side. A substantially U-shaped engagement groove 96 is disposed along an edge of the first wall 77 closer to the base 95 from the distal tip side toward the operation unit side.

The operation unit side of the first wall 77 is provided with an elevator mounting hole 76. The elevator mounting hole 76 has a circular cross section having a diameter that fits the elevator shaft 82 of the elevator 80 described with FIGS. 13 to 17. As illustrated in FIG. 20, a flange hole 761 is disposed in a joining area between the base 95 and the first wall 77 on the operation unit side.

As illustrated in FIG. 21, the flange hole 761 in the base 95 is a rectangular hole disposed in the pedestal 70 disposed along the edge on the side where the first wall 77 rises. The long side of the flange hole 761 has a length substantially equal to a diameter of the elevator mounting hole 76. The short side of the flange hole 761 has a length that allows insertion of the flange 85. A length from one edge of the base 95 to the center of the elevator mounting hole 76 is substantially equal to a length from one edge of the base 95 to the central portion of the flange hole 761 in the longitudinal direction.

As illustrated in FIG. 19, an edge of the flange hole 761 disposed in the first wall 77 has both ends protruding toward the elevator mounting hole 76. Note that the flange hole 761 may have a linear edge.

As illustrated in FIG. 20, the lateral face fixing protrusion 74 protrudes toward the opposite side of the first wall 77 from an end portion of the base 95 on the operation unit side. A chamfer, or what is called an R-chamfer, is formed on an edge of the lateral face fixing protrusion 74 on the distal tip side. The edge of the lateral face fixing protrusion 74 on the distal tip side may be what is called a C-chamfer.

Figure 22:
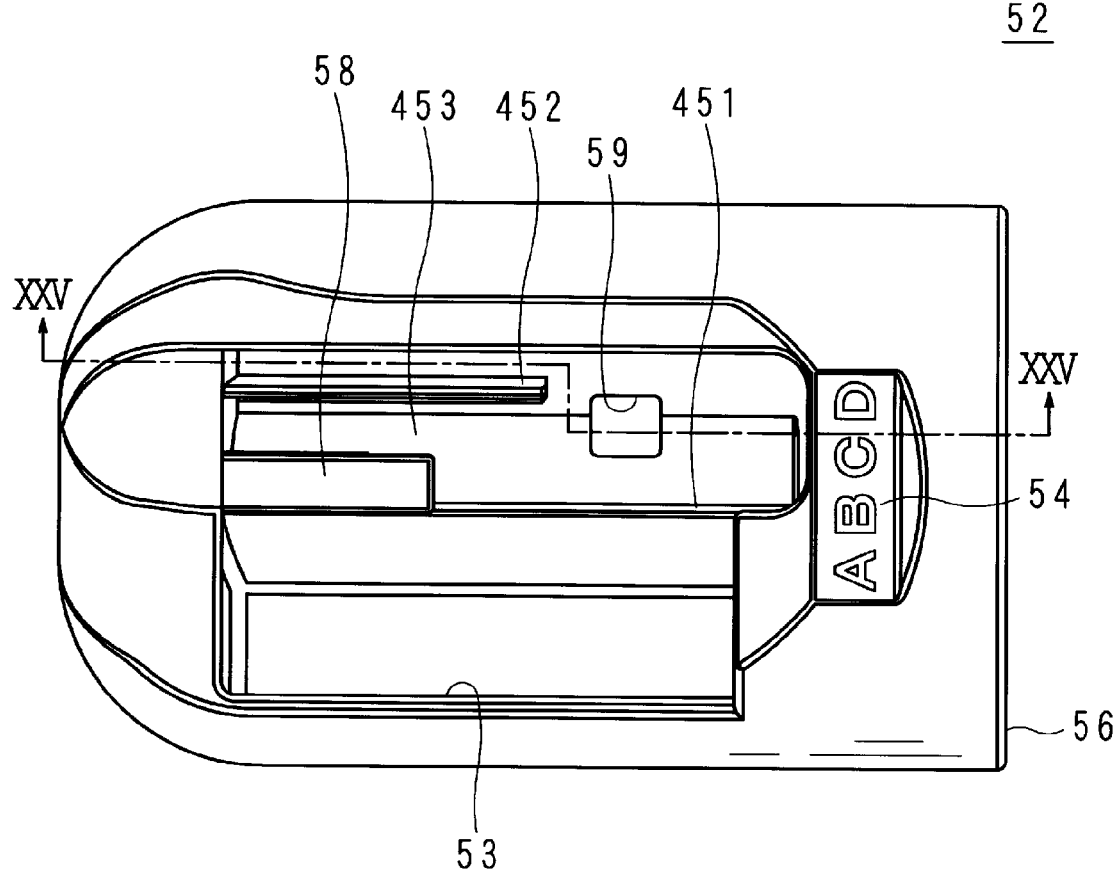
FIG. 22 is a front view of a cover.
Figure 23:
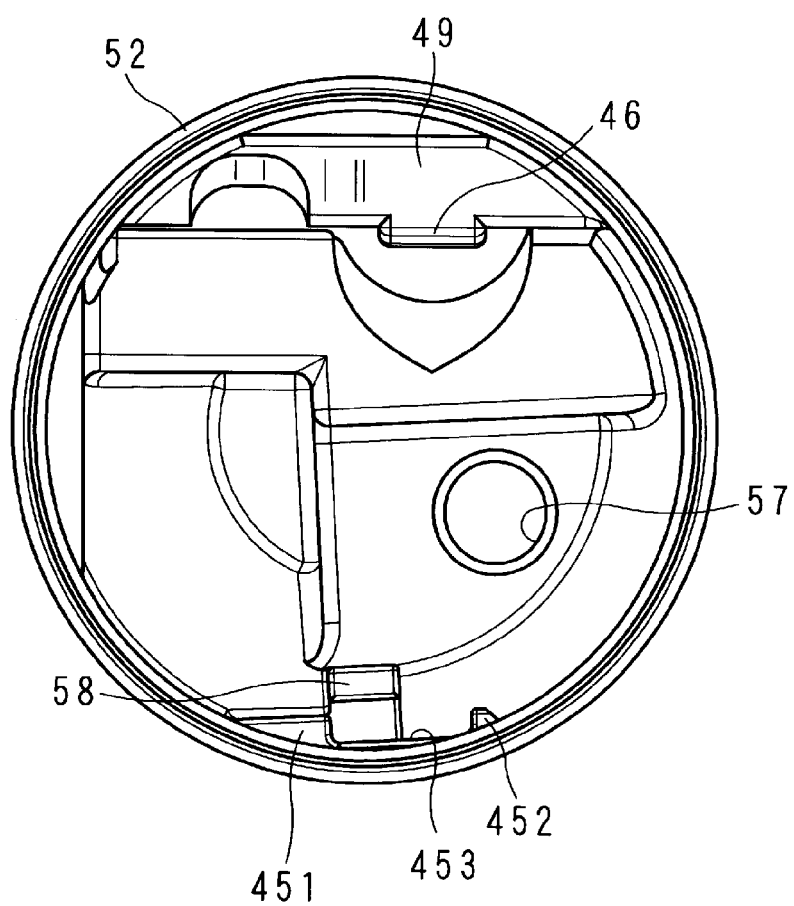
FIG. 23 is a view of the cover as seen from the side where the cover is to be mounted on the endoscope.

FIG. 22 is a front view of the cover 52. FIG. 23 is a view of the cover 52 as seen from the side where the cover 52 is to be mounted on the endoscope 10. The configuration of the cover 52 will be described with reference to FIGS. 10 to 12, 22, and 23.

As described above, the cover 52 is a cylinder with a bottom and includes the window 53 opened over almost the entire length at one place on the periphery of the cover 52. Furthermore, the cover 52 includes a pedestal fixing hole 57. The pedestal fixing hole 57 is an example of a first fixing hole of this embodiment. As illustrated in FIG. 12, the pedestal fixing hole 57 is a stepped through-hole disposed in the bottom of the cover 52 and has an outer diameter larger than an inner diameter.

As illustrated in FIGS. 22 and 23, a first pedestal support 451 and a second pedestal support 452, or stripes parallel to the axial direction of the cover 52, are disposed opposite the window 53. A flat pedestal positioning surface 453 is disposed between the first pedestal support 451 and the second pedestal support 452. An interval between the first pedestal support 451 and the second pedestal support 452 corresponds to a width of the base 95 disposed in the pedestal 70 described with reference to FIGS. 18 to 21.

The second fixing hole 59 penetrates the side closer to the opening end portion 56 than the second pedestal support 452. The cross section of the second fixing hole 59 is substantially rectangular.

A second fixing protrusion 58 having a quadrangular prism shape protrudes inward from the bottom of the cover 52. The second fixing protrusion 58 is disposed between the window 53 and the pedestal positioning surface 453. An interval corresponding to a thickness of the base 95 is disposed between the second fixing protrusion 58 and the pedestal positioning surface 453. The second fixing protrusion 58 has a size designed to be inserted into the engagement groove 96 disposed in the pedestal 70 described with reference to FIGS. 18 to 21.

As illustrated in FIGS. 11 and 23, the cover 52 includes a tabular protrusion 49 that protrudes inward along an edge of the window 53 closer to the opening end portion 56. A distal tip of the protrusion 49 is partially provided with a first engagement portion 46 that protrudes inward.

The configuration of the endoscope cap 50 will be described with reference to FIGS. 8 to 23. As illustrated in FIG. 12, the first fixing protrusion 73 is inserted into the pedestal fixing hole 57 from the inside of the cover 52. The first fixing protrusion 73 does not fall off the pedestal fixing hole 57 by the action of the lock disposed in the first fixing protrusion 73.

As illustrated in FIG. 9, the base 95 is sandwiched between the first pedestal support 451 and the second pedestal support 452. Accordingly, the pedestal 70 does not rotate around the first fixing protrusion 73. As illustrated in FIG. 10, the second fixing protrusion 58 is inserted into the engagement groove 96, and the end portion of the base 95 is sandwiched between an inner surface of the cover 52 and the second fixing protrusion 58.

As described above with reference to FIG. 11, the lateral face fixing protrusion 74 penetrates the second fixing hole 59. An end face of the lateral face fixing protrusion 74 on the operation unit side abuts against an inner surface of the second fixing hole 59. The pedestal 70 is desirably biased toward the distal tip side by the abutting portion.

The pedestal 70 may be fixed to the cover 52 by adhesion, welding, or the like. In this case, there may be a gap between the end face of the lateral face fixing protrusion 74 on the operation unit side and the inner surface of the second fixing hole 59. It is possible to achieve the endoscope cap 50 with the pedestal 70 being firmly held.

As illustrated in FIGS. 9 and 10, the elevator shaft 82 is inserted into the elevator mounting hole 76. The flange 85 is inserted into the flange hole 761. The elevator 80 is rotatable about the elevator shaft 82 supported by the elevator mounting hole 76. As illustrated in FIG. 11, when the elevator 80 is not raised, the lever connection portion 81 is opened toward the opening end portion 56.

As described with reference to FIG. 5, the endoscope cap 50 is pushed into the distal tip of the insertion portion 30. Accordingly, the elevator connection portion 61 and the lever connection portion 81 are engaged, and the first engagement portion 46 and the third engagement portion 29 are also engaged. In this manner, the endoscope cap 50 is mounted to the distal tip of the insertion portion 30.

As described with reference to FIG. 7, when a user operates the elevation control lever 21, the lever 60 rotates. Along with the rotation of the lever 60, the elevator connection portion 61 rotates, and the elevator 80 rises as indicated by the imaginary line in FIG. 11.

Figure 24:
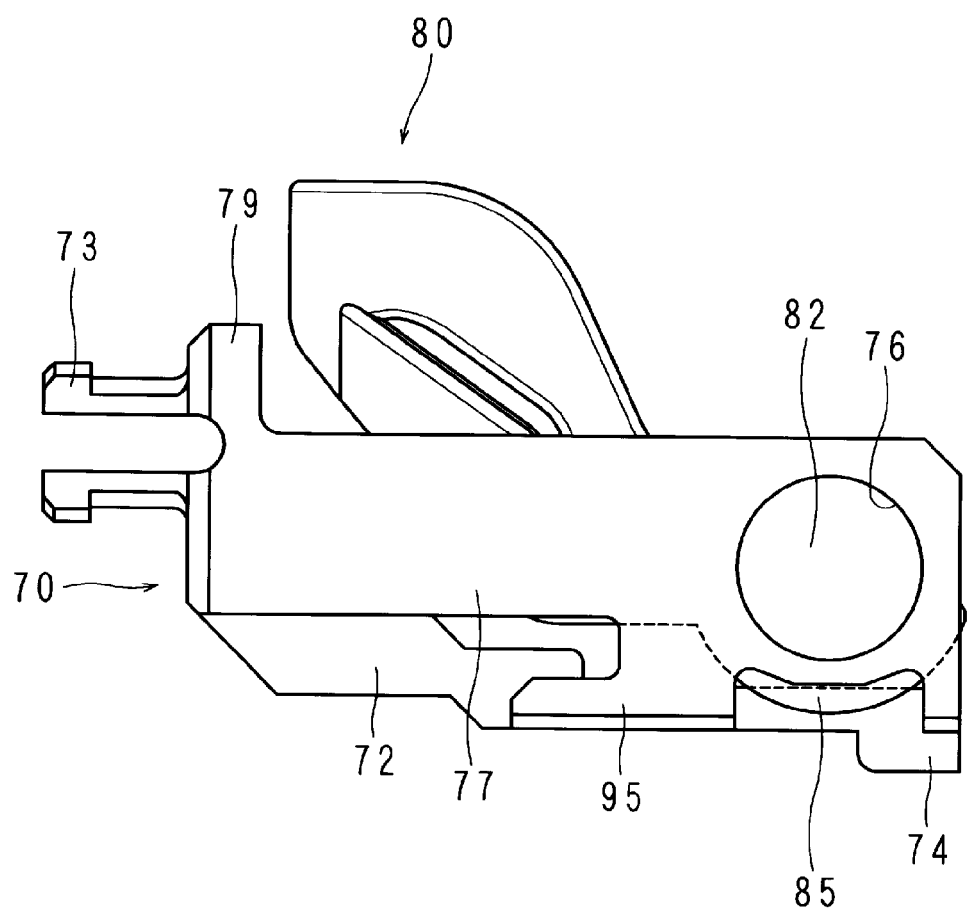
FIG. 24 is a view for describing a state where the pedestal and the elevator are assembled.

FIG. 24 is a view for describing a state where the pedestal 70 and the elevator 80 are assembled. The elevator shaft 82 is inserted into the elevator mounting hole 76, and the elevator 80 is supported by the pedestal 70, being rotatable about the elevator shaft 82.

The flange 85 is inserted into the flange hole 761. Even when a force is applied in a direction perpendicular to the paper surface of FIG. 24, the elevator 80 does not come off the pedestal 70. In other words, the flange 85 functions as a lock to prevent the elevator 80 from falling off the pedestal 70.

Figure 25:
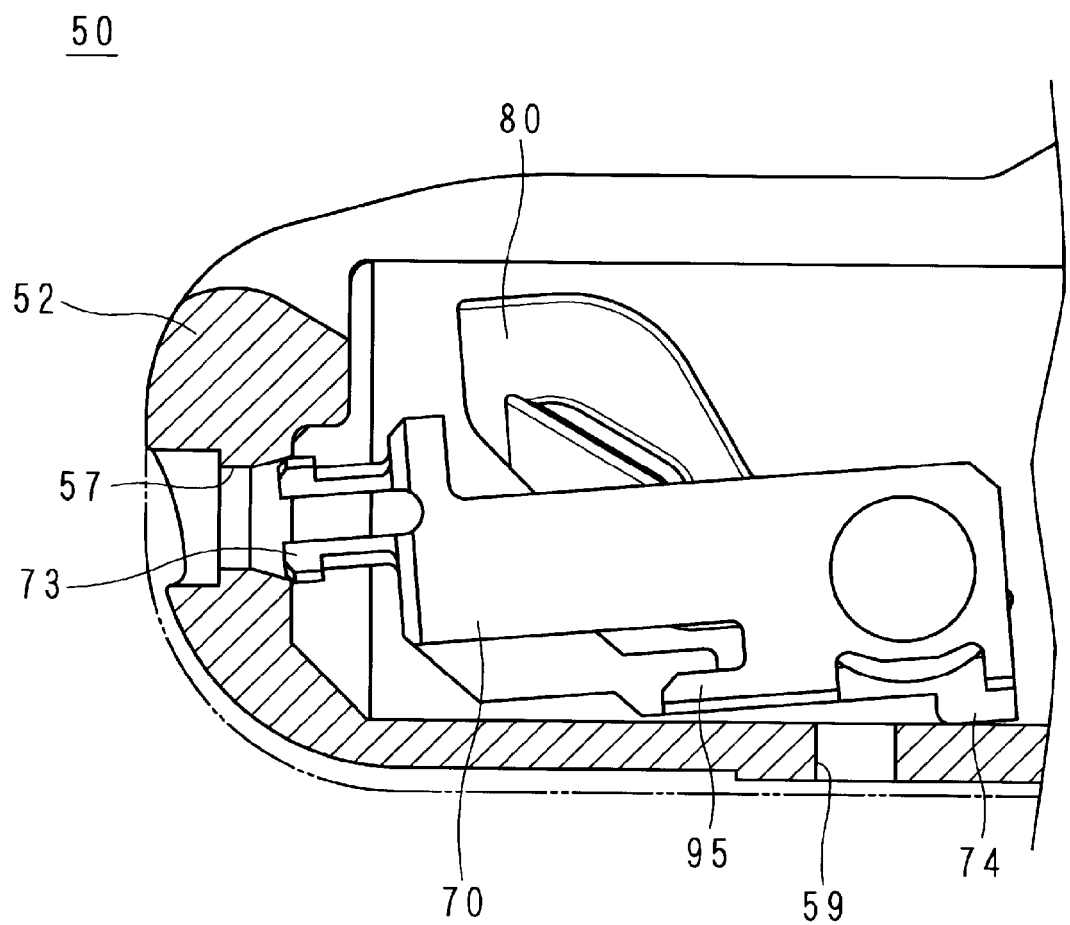
FIG. 25 is a view for describing a method for assembling the cover and the pedestal.
Figure 26:
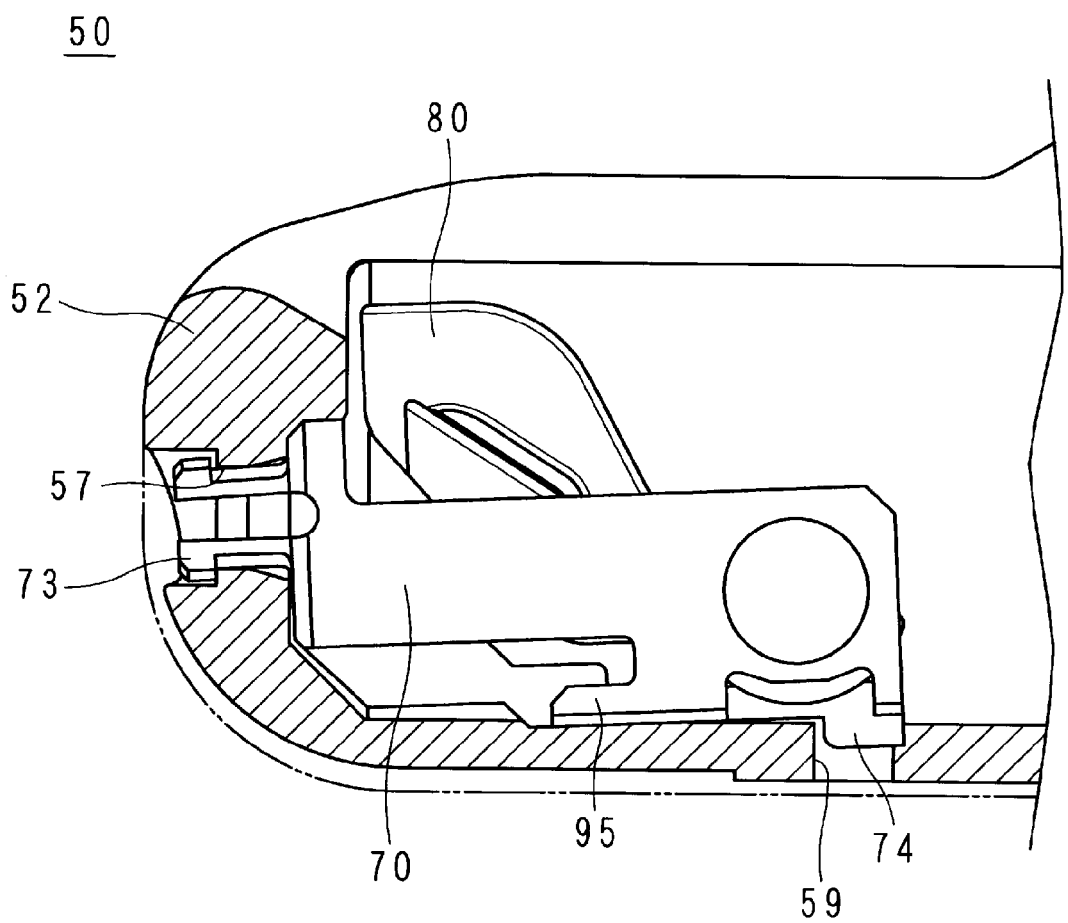
FIG. 26 is a view for describing a method for assembling the cover and the pedestal.
Figure 27:
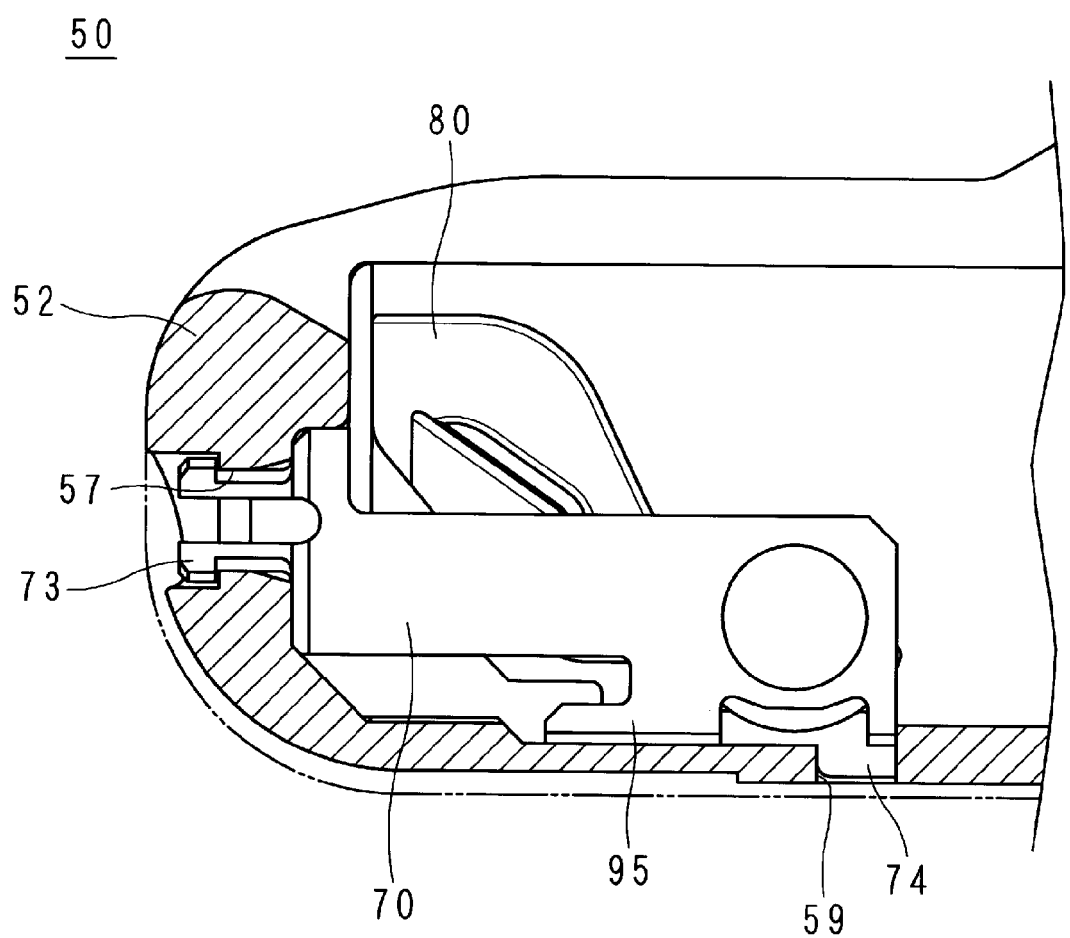
FIG. 27 is a view for describing a method for assembling the cover and the pedestal.

FIGS. 25 to 27 are views for describing a method for assembling the cover 52 and the pedestal 70. In FIGS. 25 to 27, the cover 52 and the pedestal 70 are illustrated in a front view similar to FIG. 24, and the cover 52 is illustrated in a cross-sectional view taken along a plane similar to FIG. 12. The illustration of elastic deformation during assembly is omitted.

The pedestal 70 and the elevator 80 are inserted into the cover 52 from the first fixing protrusion 73 as illustrated in FIG. 25. A distal tip of the first fixing protrusion 73 is brought into contact with an edge of the pedestal fixing hole 57. Since the lateral face fixing protrusion 74 protrudes, the base 95 is in a state where the operation unit side rises toward the center of the cover 52.

The pedestal 70 is pushed as illustrated in FIG. 26. While the slit of the first fixing protrusion 73 is closed by elastic deformation, the slit passes through the small-diameter portion of the pedestal fixing hole 57. The base 95 and the cover 52 also elastically deform, and the lateral face fixing protrusion 74 enters the second fixing holes 59. FIG. 26 does not illustrate a state where the base 95 and the cover 52 are elastically deformed. Since the edge of the lateral face fixing protrusion 74 on the distal tip side is chamfered as described above, the lateral face fixing protrusion 74 is hardly caught at an edge of the second fixing hole 59.

After that, the first fixing protrusion 73 returns to its original shape by resilience, and the lock at the distal tip becomes functional. Simultaneously, the pedestal 70 is drawn toward the bottom of the cover 52, and the lateral face fixing protrusion 74 is engaged with the second fixing hole 59 as illustrated in FIG. 27. In this manner, the endoscope cap 50 is accomplished.

According to this embodiment, the end face of the lateral face fixing protrusion 74 on the operation unit side abuts against the inner surface of the second fixing hole 59. A frictional force acting on the abutting portion prevents the cover 52 and the pedestal 70 from coming off due to an impact or the like during transportation or storage.

Since the pedestal 70 is biased toward the distal tip side by the abutting portion, the cover 52 and the pedestal 70 are prevented from coming off more effectively.

According to this embodiment, it is possible to provide the endoscope cap 50 including the cover 52 and the pedestal 70 that hardly come off when the endoscope cap 50 is mounted on or dismounted from the distal tip 31.

The engagement between the first fixing protrusion 73 and the pedestal fixing hole 57 and the engagement between the lateral face fixing protrusion 74 and the second fixing hole 59 are both performed by pushing the pedestal 70 toward the bottom of the cover 52. Accordingly, it is possible to provide the endoscope cap 50 that is easy to assemble. Due to the easiness in assembly, it is possible to provide the endoscope cap 50 preferable for mass production, that is, for one-time use.

Technical features (constitutional requirements) described in the embodiments can be combined with each other, and new technical features can be formed by the combination.

The embodiments herein are disclosed for purposes of illustration in all respects and not limitation. The scope of this invention is defined not by the aforementioned significance but by the claims and intended to include all modifications within the significance and scope equivalent to the claims.

REFERENCE SIGNS LIST

10 Endoscope
12 Soft portion
13 Bending section
20 Operation unit
21 Elevation control lever
22 Channel inlet
23 Bending knob
24 Elevation wire
29 Third engagement portion
30 Insertion portion
31 Distal tip
321 First flat surface
322 Second flat surface
323 Third flat surface
33 Optical housing portion
34 Channel
35 Channel outlet
36 Observation window
37 Lighting window
38 Nozzle
40 Treatment tool
41 Treatment tool distal tip
451 First pedestal support
452 Second pedestal support
453 Pedestal positioning surface
46 First engagement portion
49 Protrusion
50 Endoscope cap
52 Cover
53 Window
54 Sign display
56 Opening end portion
57 Pedestal fixing hole (first fixing hole)
58 Second fixing protrusion
59 Second fixing hole
60 Lever
61 Elevator connection portion
64 Rotatable connection portion
65 Wire anchor 66 Lid screw
67 Lever chamber lid
68 Support wall
69 Lever chamber
70 Pedestal
73 First fixing protrusion (bottom fixing protrusion)
74 Lateral face fixing protrusion
76 Elevator mounting hole
761 Flange hole
77 First wall (support wall)
78 Second wall
79 Third wall (distal tip wall)
80 Elevator
81 Lever connection portion
82 Elevator shaft
83 Raiser
831 First raiser
832 Second raiser
84 Recess
85 Flange
95 Base
96 Engagement groove

The invention claimed is:

1. An endoscope cap detachably attached to an insertion portion of an endoscope, the endoscope cap comprising:
a cover having a cylindrical shape with a bottom, and being detachably attached to a distal tip of the insertion portion from an opening end portion;
a pedestal held inside the cover; and
an elevator rotatably supported by the pedestal,
wherein the pedestal includes:
 a base having a tabular shape, being disposed in an inner surface of a cylindrical portion of the cover;
 a support wall having a tabular shape, rising from an edge of the base, and extending in an axial direction of the cover to support the elevator;
 a distal tip wall extending from a distal tip of the support wall in the same direction as the base;
 a bottom fixing protrusion protruding from the distal tip wall in a direction opposite to the support wall; and
 a lateral face fixing protrusion outwardly protruding from the base in a radial direction opposite to the support wall, and
the cover includes:
 a first fixing hole into which the bottom fixing protrusion is inserted, the first fixing hole being disposed in the bottom; and
 a second fixing hole into which the lateral face fixing protrusion is inserted, the second fixing hole being disposed in a lateral face surface of the cover along an axial direction of the cover.

2. The endoscope cap according to claim 1,
wherein the lateral face fixing protrusion is disposed at an edge of the base opposite to a direction in which the support wall extends.

3. The endoscope cap according to claim 1,
wherein the lateral face fixing protrusion includes a chamfer at an edge closer to the bottom fixing protrusion.

4. The endoscope cap according to claim 3,
wherein the chamfer is an R-chamfer.

5. The endoscope cap according to claim 1,
wherein the pedestal has an elevator mounting hole penetrating the support wall, and
the elevator includes:
an elevator shaft inserted into the elevator mounting hole; and
a lever connection portion connected to a lever rotatably disposed at the distal tip of the insertion portion.

6. The endoscope cap according to claim 1,
wherein the base includes a flange hole disposed at an edge of the support wall, and
the elevator includes a tabular flange inserted into the flange hole.

7. An endoscope comprising:
an elevator connection portion rotatably exposed at a surface of a distal tip of an insertion portion; and
an endoscope cap including: a cover having a cylindrical shape with a bottom, and being detachably attached to the distal tip of the insertion portion from an opening end portion; a pedestal held inside the cover; and an elevator rotatably supported by the pedestal, including a lever connection portion connected to the elevator connection portion, the pedestal including: a base having a tabular shape, being disposed in an inner surface of a cylindrical portion of the cover; a support wall having a tabular shape, rising from an edge of the base, and extending in an axial direction of the cover to support the elevator; a distal tip wall extending from a distal tip of the support wall in the same direction as the base; a bottom fixing protrusion protruding from the distal tip wall in a direction opposite to the support wall; and a lateral face fixing protrusion outwardly protruding from the base in a radial direction, the cover including: a first fixing hole into which the bottom fixing protrusion is inserted, the first fixing hole being disposed in the bottom; and a second fixing hole into which the lateral face fixing protrusion is inserted, the second fixing hole being disposed in a surface of the cover along an axial direction of the cover.

* * * * *